US010745347B2

(12) United States Patent
Allen et al.

(10) Patent No.: US 10,745,347 B2
(45) Date of Patent: *Aug. 18, 2020

(54) UNSATURATED FATTY ALCOHOL DERIVATIVES FROM NATURAL OIL METATHESIS

(71) Applicant: Stepan Company, Northfield, IL (US)

(72) Inventors: David R. Allen, Chicago, IL (US); Marcos Alonso, Chicago, IL (US); Mary Beddaoui, Glenview, IL (US); Randal J. Bernhardt, Antioch, IL (US); Aaron Brown, Chicago, IL (US); Scott Dillavou, Skokie, IL (US); Xue Min Dong, Lincolnshire, IL (US); Wilma Gorman, Park Ridge, IL (US); John C. Hutchison, Chicago, IL (US); Gary Luebke, Chicago, IL (US); Renee Luka, Park Ridge, IL (US); Franz Luxem, Palatine, IL (US); Andrew D Malec, Chicago, IL (US); Ronald A. Masters, Glenview, IL (US); Dennis S. Murphy, Libertyville, IL (US); Nicholas Pendleton, Atlanta, GA (US); Irma Ryklin, Buffalo Grove, IL (US); Patti Skelton, Winder, GA (US); Brian Sook, Valdosta, GA (US); Chris Spaulding, Evanston, IL (US); Krista Turpin, Loganville, GA (US); Gregory Wallace, Chicago, IL (US); Michael Wiester, Chicago, IL (US); Patrick Shane Wolfe, Palatine, IL (US)

(73) Assignee: STEPAN COMPANY, Northfield, IL (US)

( * ) Notice: Subject to any disclaimer, the term of this patent is extended or adjusted under 35 U.S.C. 154(b) by 573 days.

This patent is subject to a terminal disclaimer.

(21) Appl. No.: 14/395,835

(22) PCT Filed: Mar. 13, 2013

(86) PCT No.: PCT/US2013/031049
§ 371 (c)(1),
(2) Date: Oct. 21, 2014

(87) PCT Pub. No.: WO2013/162736
PCT Pub. Date: Oct. 31, 2013

(65) Prior Publication Data
US 2015/0087521 A1 Mar. 26, 2015

Related U.S. Application Data

(60) Provisional application No. 61/637,607, filed on Apr. 24, 2012.

(51) Int. Cl.
C07C 309/10 (2006.01)
C07C 29/147 (2006.01)
C07C 309/08 (2006.01)
A01N 25/30 (2006.01)
B01F 17/00 (2006.01)
C11D 1/37 (2006.01)
C04B 38/10 (2006.01)
C07C 303/32 (2006.01)
(Continued)

(52) U.S. Cl.
CPC .......... C07C 309/10 (2013.01); A01N 25/30 (2013.01); A61K 8/463 (2013.01); A61K 8/466 (2013.01); B01F 17/0057 (2013.01); B01F 17/0092 (2013.01); C04B 38/10 (2013.01); C07C 29/147 (2013.01); C07C 41/06 (2013.01); C07C 303/14 (2013.01); C07C 303/32 (2013.01); C07C 309/08 (2013.01); C09D 7/63 (2018.01); C11D 1/143 (2013.01); C11D 1/146 (2013.01); C11D 1/29 (2013.01); C11D 1/37 (2013.01); C11D 1/66 (2013.01); A61K 2800/10 (2013.01)

(58) Field of Classification Search
None
See application file for complete search history.

(56) References Cited

U.S. PATENT DOCUMENTS 1,981,901 A   11/1934  Mills et al.
2,199,403 A *  5/1940  Henke ................... C07C 305/14
                                                     558/36

(Continued)

FOREIGN PATENT DOCUMENTS

CN   1784202 A    6/2006
DE   1467230 A1   1/1969
(Continued)

OTHER PUBLICATIONS

Jaeger,D. A.; Sayed, Y. M. "Synthesis and Characterization of Single-chain second generation cleavable surfactants" J. Org. Chem., 1993, 58, 2619-2627.*

(Continued)

Primary Examiner — Erin E Hirt
(74) Attorney, Agent, or Firm — Dilworth IP, LLC

(57) ABSTRACT

Sulfate and sulfonate derivatives of unsaturated fatty alcohols, processes for making them, and methods of using them are disclosed. In one aspect, a monounsaturated fatty alcohol composition is made by reducing a metathesis-derived monounsaturated alkyl ester. The fatty alcohol composition is then converted to a sulfate or sulfonate derivative by one or more of alkoxylation, sulfation, sulfonation, and sulfitation. Of particular interest are the sulfate and ether sulfate derivatives.

5 Claims, No Drawings

(51) Int. Cl.

| | | |
|---|---|---|
| *C07C 303/14* | (2006.01) | |
| *C09D 7/63* | (2018.01) | |
| *A61K 8/46* | (2006.01) | |
| *C11D 1/14* | (2006.01) | |
| *C11D 1/29* | (2006.01) | |
| *C07C 41/06* | (2006.01) | |
| *C11D 1/66* | (2006.01) | |

(56) References Cited

U.S. PATENT DOCUMENTS

| | | | |
|---|---|---|---|
| 2,653,970 A | 9/1953 | Fessler | |
| 2,865,968 A | 12/1958 | Hansley et al. | |
| 2,875,125 A * | 2/1959 | Gaertner | C07C 311/37 |
| | | | 504/244 |
| 3,169,142 A | 2/1965 | Knaggs | |
| 3,193,586 A | 7/1965 | Rittmeister | |
| 3,256,155 A * | 6/1966 | Cahn | A61K 8/463 |
| | | | 424/56 |
| 3,544,613 A | 12/1970 | Knaggs | |
| 3,875,202 A | 4/1975 | Steckler | |
| 3,896,057 A | 7/1975 | Lindsay et al. | |
| 4,087,457 A | 5/1978 | Conyers et al. | |
| 4,148,821 A | 4/1979 | Nussbaum | |
| 4,275,013 A | 6/1981 | Tokosh | |
| 4,545,941 A | 10/1985 | Rosenburg | |
| 4,804,790 A | 2/1989 | Schuett | |
| 5,096,616 A * | 3/1992 | Kittle | B01F 5/102 |
| | | | 252/3 |
| 5,124,491 A | 6/1992 | Fleckenstein et al. | |
| 5,312,940 A | 5/1994 | Grubbs et al. | |
| 5,342,909 A | 8/1994 | Grubbs et al. | |
| 5,446,188 A | 8/1995 | Gruber | |
| 5,482,908 A | 1/1996 | Le-Khac | |
| 5,672,781 A | 9/1997 | Koehler et al. | |
| 5,710,298 A | 1/1998 | Grubbs et al. | |
| 5,728,785 A | 3/1998 | Grubbs et al. | |
| 5,728,917 A | 3/1998 | Grubbs et al. | |
| 5,750,815 A | 5/1998 | Grubbs et al. | |
| 5,831,108 A | 11/1998 | Grubbs et al. | |
| 5,922,863 A | 7/1999 | Grubbs et al. | |
| 6,306,988 B1 | 10/2001 | Grubbs et al. | |
| 6,414,097 B1 | 7/2002 | Grubbs et al. | |
| 6,683,224 B1 | 1/2004 | Hourticolon et al. | |
| 6,696,597 B2 | 2/2004 | Pederson et al. | |
| 6,746,988 B2 * | 6/2004 | Hopkinson | A01N 25/30 |
| | | | 504/127 |
| 6,794,534 B2 | 9/2004 | Grubbs et al. | |
| 7,102,047 B2 | 9/2006 | Grubbs et al. | |
| 7,169,959 B2 | 1/2007 | Heck et al. | |
| 7,208,643 B2 | 4/2007 | Namba et al. | |
| 7,378,528 B2 | 5/2008 | Herrmann et al. | |
| 7,968,742 B2 | 6/2011 | Aigner et al. | |
| 8,481,747 B2 | 7/2013 | Schrodi | |
| 8,501,973 B2 | 8/2013 | Schrodi et al. | |
| 8,569,560 B2 | 10/2013 | Schrodi et al. | |
| 8,614,344 B2 | 12/2013 | Kaido et al. | |
| 8,735,640 B2 | 5/2014 | Cohen et al. | |
| 2005/0170968 A1 | 8/2005 | Berghaus et al. | |
| 2009/0264672 A1 | 10/2009 | Abraham et al. | |
| 2010/0145086 A1 | 6/2010 | Schrodi et al. | |
| 2010/0282467 A1 | 11/2010 | Hutchison et al. | |
| 2010/0303739 A1 | 12/2010 | Spoerer et al. | |
| 2010/0310483 A1 | 12/2010 | Klug et al. | |
| 2010/0311625 A1 | 12/2010 | Elomari et al. | |
| 2011/0028374 A1 | 2/2011 | Fossum et al. | |
| 2011/0098492 A1 | 4/2011 | Varineau et al. | |
| 2011/0113679 A1 | 5/2011 | Cohen et al. | |
| 2012/0035386 A1 | 2/2012 | Nguyen et al. | |
| 2012/0058067 A1 | 3/2012 | van Gogh et al. | |
| 2013/0281688 A1 | 10/2013 | Di Biase et al. | |
| 2014/0275506 A1 | 9/2014 | Littich et al. | |
| 2014/0336398 A1 | 11/2014 | Cohen et al. | |
| 2014/0336399 A1 | 11/2014 | Cohen et al. | |

FOREIGN PATENT DOCUMENTS

| | | | | |
|---|---|---|---|---|
| DE | 19806221 A1 * | 8/1999 | | C07C 29/80 |
| GB | 1426408 A * | 2/1976 | | A61K 8/24 |
| WO | 9113057 | 9/1991 | | |
| WO | 9113057 A1 | 9/1991 | | |
| WO | 2008048522 | 4/2008 | | |
| WO | 2012061092 | 5/2012 | | |
| WO | 2012061093 | 5/2012 | | |
| WO | 2012061095 | 5/2012 | | |

OTHER PUBLICATIONS

Hill, A. S. et al. "Nantucket Pine tip moth, Rhyacionia frustrana: Identification of two sex pheromone components" Journal of Chemical Ecology, 1981, 7(3), 517-528 (Year: 1981).*
Subrahmanyam, V.V.R. et al.: "Structure and Surfactance-Evaluation of Ricinoleyl Alcohol", Journal of Chemical & Engineering Data, vol. 6, No. 1, Jan. 1, 1961), pp. 38-42, XP-002744452.
Rzymskowski, J. et al.: "Preparation of water-in-oil emulsions in presence of ethanol", Pharmazie (1947), vol. 2, pp. 509-510, XP-002744453.
Cormier, J. et al.: "An alternative synthesis and mobile phase ion chromatography of alkanedisulfates", Journal of Surfactants and Detergents (2002), vol. 5, No. 4, pp. 359-362, XP-002744454.
Pittelkow, M., et al: "Molecular recognition: Comparative study of a tunable host-guest system by using a fluorescent model system and collision-induced dissociation mass spectrometry on dendrimers", Chemistry—A European Journal (2005), vol. 11, No. 17, pp. 5126-5135, XP-002744455.
Parera, E. et al.: "New Surfactant Phosphine Ligands and Platinum (II) Metallosurfactants, Influence of Metal Coordination on the Critical Micelle Concentration and Aggregation Properties", Langmuir (2010), vol. 26, No. 2, pp. 743-751, XP002744456.
Carmona, I. et al: "Synthesis and performance of linear monoisomeric ethylene oxide sulfonate", Journal of Dispersion Science and Technology (1983), vol. 4, No. 4, pp. 361-370, XP-002744485.
Weil, J. et al.: "Ether alcohol sulfates from oleyl alcohol", Journal of the American Oil Chemists' Society (1967), vol. 44, No. 9, pp. 522-524, XP-002744486.
"Supplementary EP Search Report" dated Jan. 25, 2016 issued by the European Patent Office in corresponding EP Application No. 13780515, 19 pages.
J.C. Mol, Green Chem. 4 (2002) 5.
J.C. Mol, Topics in Catal. 27 (2004) 97.
Dijgoué et al., Appl. Catal. A 368 (2009) 158.
R. Subbarao et al., Indian J. Tech. 4 (1966) 153.
Chinese Office Action dated Sep. 2, 2016 and Searcgh Report issued by SIPO in corresponding CN Application No. 201380033623.2, along with unofficial English translation, 32 pages.
Youn, M. et al.: "The additive effect of polyoxethylene compounds on the photographic characters of photographic emulsion", Journal of Photoscience (2000), p. 45-46.
Baumann, W. et al: "Alkoxylipids IV. Synthesis and Characterization of Naturally Occurring Ethers, Esters and Ether Esters of Diols", Biochimica et Biophysica ACTA, Jan. 1, 1967, pp. 355-365 (abstract only).
Dierker, M. et al: "Surfactants from oleic, erucic and petroselinic acid: Synthesis and properties", European Journal of Lipid Science and Technology, vol. 112, No. 1, Jan. 2010, pp. 122-135 (abstract only).
M. R. Sad, V.A. Mazzieri C.R. Vera and C.L. Pieck, "Hidrogenación selectiva de metil ésteres de ácidos grasos para obtención de alcoholes grasos. I. Perspectivas actuales, catalizadores y mecanismos de reacción", Advances in Chemistry, 2 (2), 17-24 (2007) (abstract only).
"Sulfated/Sulfonated Product of Unsaturated Alcohols and the Ethers thereof", XU Changqing, China Surfactant Detergent & Cosmetics, No. 1, pp. 23-28, published on Mar. 1, 1992.
"Catalytic Disproportionation—A New Method for Oleochemical", Yao Jinshui, et al., China Oils and Fats, No. 2, vol. 24, pp. 0-2, published on Apr. 25, 1999.

* cited by examiner

UNSATURATED FATTY ALCOHOL DERIVATIVES FROM NATURAL OIL METATHESIS

FIELD OF THE INVENTION

The invention generally relates to unsaturated fatty alcohol derivatives wherein the unsaturated fatty alcohols are made from a metathesis-derived feedstock.

BACKGROUND OF THE INVENTION

Fatty alcohol derivatives, particularly sulfates and ether sulfates, are versatile surfactants. They are used across a broad array of industries and end uses, including personal care, laundry and cleaning, emulsion polymerization, agricultural uses, oilfield applications, industrial compositions, and specialty foamers.

Fatty alcohols are usually made by reducing the corresponding fatty acids or esters, typically by catalytic hydrogenation. Often, the catalyst includes zinc or copper and chromium. U.S. Pat. No. 5,672,781, for instance, uses a $CuCrO_4$ catalyst to hydrogenate methyl esters from palm kernel oil, which has substantial unsaturation, to produce a mixture of fatty alcohols comprising about 52 wt. % of oleyl alcohol, a monounsaturated fatty alcohol. For additional examples, see U.S. Pat. Nos. 2,865,968; 3,193,586; 4,804,790; 6,683,224; and 7,169,959.

The fatty acids or esters used to make fatty alcohols and their derivatives are usually made by hydrolysis or transesterification of triglycerides, which are typically animal or vegetable fats. Consequently, the fatty portion of the acid or ester will typically have 6-22 carbons with a mixture of saturated and internally unsaturated chains. Depending on source, the fatty acid or ester often has a preponderance of $C_{16}$ to $C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. The unsaturation in these acids has either exclusively or predominantly cis-configuration.

Recent improvements in metathesis catalysts (see J. C. Mol, Green Chem. 4 (2002) 5) provide an opportunity to generate reduced chain length, monounsaturated feedstocks, which are valuable for making detergents and surfactants, from $C_{16}$ to $C_{22}$-rich natural oils such as soybean oil or palm oil. Soybean oil and palm oil can be more economical than, for example, coconut oil, which is a traditional starting material for making detergents. Metathesis relies on conversion of olefins into new products by rupture and reformation of carbon-carbon double bonds mediated by transition metal carbene complexes. Self-metathesis of an unsaturated fatty ester can provide an equilibrium mixture of starting material, an internally unsaturated hydrocarbon, and an unsaturated diester. For instance, methyl oleate (methyl cis-9-octadecenoate) is partially converted to 9-octadecene and dimethyl 9-octadecene-1,18-dioate, with both products consisting predominantly of the trans-isomer. Metathesis effectively isomerizes the cis-double bond of methyl oleate to give an equilibrium mixture of cis- and trans-isomers in both the "unconverted" starting material and the metathesis products, with the trans-isomers predominating.

Cross-metathesis of unsaturated fatty esters with olefins generates new olefins and new unsaturated esters that can have reduced chain length and that may be difficult to make otherwise. For instance, cross-metathesis of methyl oleate and 3-hexene provides 3-dodecene and methyl 9-dodecenoate (see also U.S. Pat. No. 4,545,941). Terminal olefins are particularly desirable synthetic targets, and Elevance Renewable Sciences, Inc. recently described an improved way to prepare them by cross-metathesis of an internal olefin and an α-olefin in the presence of a ruthenium alkylidene catalyst (see U.S. Pat. Appl. Publ. No. 2010/0145086). A variety of cross-metathesis reactions involving an α-olefin and an unsaturated fatty ester (as the internal olefin source) are described. Thus, for example, reaction of soybean oil with propylene followed by hydrolysis gives, among other things, 1-decene, 2-undecenes, 9-decenoic acid, and 9-undecenoic acid. Despite the availability (from cross-metathesis of natural oils and olefins) of unsaturated fatty esters having reduced chain length and/or predominantly trans-configuration of the unsaturation, sulfated and sulfonated derivatives of the unsaturated fatty alcohols appear to be unknown.

In sum, traditional sources of fatty acids and esters used for making unsaturated fatty alcohols and their sulfate and ether sulfate derivatives generally have predominantly (or exclusively) cis-isomers and lack relatively short-chain (e.g., $C_{10}$ or $C_{12}$) unsaturated fatty portions. Metathesis chemistry provides an opportunity to generate precursors having shorter chains and mostly trans-isomers, which could impart improved performance when the precursors are converted to downstream compositions (e.g., in surfactants).

Sulfation of alcohols produces alcohol sulfates, which have an $C-O-SO_3X$ group, where X is typically an alkali metal or ammonium ion from a subsequent neutralization step. Sulfonation of unsaturated hydrocarbons gives sulfonates, which have a $C-SO_3X$ group. When an unsaturated alcohol is the starting material, the unsaturated sulfate can be produced under some conditions (see, e.g., WO91/13057). With other reagents, alcohol sulfation and carbon-carbon double bond sulfonation may compete, with most of the reaction product resulting from sulfation, although the nature of the sulfonated by-products is generally not well understood (see, e.g., U.S. Pat. No. 5,446,188). Because of the competing side reactions, unsaturated alcohols are usually avoided when the goal is to make an alcohol sulfate or ether sulfate.

SUMMARY OF THE INVENTION

The invention relates to sulfate and sulfonate derivatives made by one or more of alkoxylating, sulfating, sulfonating, and sulfitating monounsaturated fatty alcohol compositions. In one aspect, the fatty alcohol compositions are obtained by reducing a metathesis-derived monounsaturated alkyl ester. Of particular interest are the sulfate and ether sulfate derivatives. Microscopy studies indicate that the unsaturated sodium sulfates in particular have a lamellar phase that should enable formulation at high actives levels.

In another aspect, the invention relates to sulfate compositions comprising 40 to 60 wt. % of a monounsaturated fatty primary alcohol sulfate and 40 to 60 wt. % of a secondary hydroxyalkyl primary alcohol sulfate.

The derivatives and sulfate compositions are valuable for many end-use applications, including, for example, agricultural dispersants, water-soluble herbicides, anionic emulsifiers for agricultural use, hard surface cleaners, light-duty liquid detergents, personal cleansers, gas well foamers for oilfield applications, laundry detergents, enhanced oil recovery compositions, latex paints, and specialty foams.

DETAILED DESCRIPTION OF THE INVENTION

In one aspect, the invention relates to sulfate or sulfonate derivatives made by one or more of alkoxylating, sulfating, sulfonating, and sulfitating monounsaturated fatty alcohol compositions. The fatty alcohol compositions are made by reducing a metathesis-derived monounsaturated alkyl ester.

The monounsaturated alkyl ester, preferably a $C_5$-$C_{35}$ alkyl ester, and more preferably a $C_{10}$-$C_{17}$ monounsaturated lower alkyl ester, used as a reactant is derived from metathesis of a natural oil. Traditionally, these materials, particularly the short-chain alkyl esters (e.g., methyl 9-decenoate or methyl 9-dodecenoate), have been difficult to obtain except in lab-scale quantities at considerable expense. However, because of the recent improvements in metathesis catalysts, these esters are now available in bulk at reasonable cost. Thus, the monounsaturated esters are conveniently generated by self-metathesis of natural oils or cross-metathesis of natural oils with olefins, preferably α-olefins, and particularly ethylene, propylene, 1-butene, 1-hexene, 1-octene, and the like.

As used herein, "monounsaturated" refers to compositions that comprise principally species having a single carbon-carbon double bond but may also include a minor proportion of one or more species that have two or more carbon-carbon double bonds. The skilled person will appreciate that it is not necessary and often impractical to produce a purely "monounsaturated" species, and that mixtures comprising principally (but not exclusively) monounsaturated esters, alcohols, and derivatives are contemplated as within the scope of the invention.

Non-limiting examples of procedures for making monounsaturated lower alkyl esters by metathesis are disclosed in WO 2008/048522, the contents of which are incorporated herein by reference. In particular, Examples 8 and 9 of WO 2008/048522 may be employed to produce methyl 9-decenoate and methyl 9-dodecenoate. Suitable procedures also appear in U.S. Pat. Appl. Publ. No. 2011/0113679 and PCT Int. Appl. Nos. WO 2012/061093 and WO 2012/061095, the teachings of which are incorporated herein by reference.

Preferably, at least a portion of the monounsaturated alkyl ester has "$\Delta^9$" unsaturation, i.e., the carbon-carbon double bond in the lower alkyl ester is at the 9-position with respect to the ester carbonyl. In other words, there are preferably seven carbons between the ester carbonyl group and the olefin group at C9 and C10. For the $C_{11}$ to $C_{17}$ esters, an alkyl chain of 1 to 7 carbons, respectively is attached to C10. Preferably, the unsaturation is at least 1 mole % trans-$\Delta^9$, more preferably at least 25 mole % trans-$\Delta^9$, more preferably at least 50 mole % trans-$\Delta^9$, and even more preferably at least 80% trans-$\Delta^9$. The unsaturation may be greater than 90 mole %, greater than 95 mole %, or even 100% trans-$\Delta^9$. In contrast, naturally sourced fatty esters that have $\Delta^9$ unsaturation, e.g., methyl oleate, usually have ~100% cis-isomers.

Although a high proportion of trans-geometry (particularly trans-$\Delta^9$ geometry) may be desirable in the metathesis-derived unsaturated fatty alcohol derivatives of the invention, the skilled person will recognize that the configuration and the exact location of the carbon-carbon double bond will depend on reaction conditions, catalyst selection, and other factors. Metathesis reactions are commonly accompanied by isomerization, which may or may not be desirable. See, for example, G. Djigoué and M. Meier, *Appl. Catal., A* 346 (2009) 158, especially FIG. 3. Thus, the skilled person might modify the reaction conditions to control the degree of isomerization or alter the proportion of cis- and trans-isomers generated. For instance, heating a metathesis product in the presence of an inactivated metathesis catalyst might allow the skilled person to induce double bond migration to give a lower proportion of product having trans-$\Delta^9$ geometry.

An elevated proportion of trans-isomer content (relative to the usual all-cis configuration of the natural monounsaturated ester) imparts different physical properties to unsaturated fatty alcohol derivatives, including, for example, modified physical form, melting range, compactability, and other important properties. These differences should allow formulators that use unsaturated fatty alcohol derivatives greater latitude or expanded choice as they use them in cleaners, detergents, personal care, agricultural uses, specialty foams, and other end uses.

Monounsaturation can also impart advantages to formulated products (including consumer products) that are often not available with the corresponding saturated fatty alcohol derivatives. Because crystallinity is disrupted by the presence of a carbon-carbon double bond, monounsaturated sulfates and ether sulfates usually have lower viscosities than their saturated analogs. Moreover, the monounsaturated sulfates and ether sulfates can be concentrated and formulated at higher actives levels—sometimes much higher—than their saturated counterparts. For instance, a saturated ether sulfate might allow a maximum 30 wt. % actives level to give a flowable liquid, whereas an otherwise similar monounsaturated ether sulfate could allow the actives level to be as high as 70 or 80 wt. %. Thus, the seemingly minor structural change to a monounsaturated product can enable shipment of more concentrated products, reduce or eliminate the need for special handling equipment, and/or ultimately provide substantial cost savings. The monounsaturated sulfates and ether sulfates are also more effective as compatibilizers for surfactants or other components in the fully formulated products.

Suitable metathesis-derived monounsaturated esters derive from carboxylic acids. Preferably, the esters derive from $C_5$-$C_{35}$ carboxylic acids, more preferably from $C_{10}$-$C_{17}$ carboxylic acids. Example include esters derived from 9-decylenic acid (9-decenoic acid), 9-undecenoic acid, 9-dodecylenic acid (9-dodecenoic acid), 9-tridecenoic acid, 9-tetradecenoic acid, 9-pentadecenoic acid, 9-hexadecenoic acid, 9-heptadecenoic acid, and the like.

Usually, cross-metathesis or self-metathesis of the natural oil is followed by separation of an olefin stream from a modified oil stream, typically by stripping or distilling out the more volatile olefins. The modified oil stream is then reacted with a lower alcohol, typically methanol, to give glycerin and a mixture of alkyl esters. This mixture normally includes saturated $C_6$-$C_{22}$ alkyl esters, predominantly $C_{16}$-$C_{18}$ alkyl esters, which are essentially spectators in the metathesis reaction. The rest of the product mixture depends on whether cross- or self-metathesis is used. When the natural oil is cross-metathesized with an α-olefin and the product mixture is transesterified, the resulting alkyl ester mixture includes a $C_{10}$ unsaturated alkyl ester and one or more $C_{11}$ to $C_{17}$ unsaturated alkyl ester coproducts in addition to the glycerin by-product. The terminally unsaturated $C_{10}$ product is accompanied by different coproducts depending upon which α-olefin(s) is used as the cross-metathesis reactant. Thus, 1-butene gives a $C_{12}$ unsaturated alkyl ester, 1-hexene gives a $C_{14}$ unsaturated alkyl ester, and so on. The unsaturated alkyl esters are readily separated from each other and easily purified by fractional distillation. These lower alkyl esters are excellent starting materials for making the inventive unsaturated alcohol derivative compositions.

Natural oils suitable for use as a feedstock to generate the monounsaturated alkyl esters from self-metathesis or cross-metathesis with olefins are well known. Suitable natural oils include vegetable oils, algal oils, animal fats, tall oils, derivatives of the oils, and combinations thereof. Thus, suitable natural oils include, for example, soybean oil, palm oil, rapeseed oil, coconut oil, palm kernel oil, sunflower oil, safflower oil, sesame oil, corn oil, olive oil, peanut oil, cottonseed oil, canola oil, castor oil, linseed oil, tung oil, jatropha oil, mustard oil, pennycress oil, camelina oil, tallow, lard, poultry fat, fish oil, and the like. Soybean oil, palm oil, rapeseed oil, and mixtures thereof are preferred natural oils.

Oils produced using bioengineered microorgranisms can be used as feedstocks. Genetically modified oils, e.g., high-oleate soybean oil or genetically modified algal oil, can also be used. Preferred natural oils have substantial unsaturation, as this provides a reaction site for the metathesis process for generating olefins. Particularly preferred are natural oils that have a high content of unsaturated fatty groups derived from oleic acid. Thus, particularly preferred natural oils include soybean oil, palm oil, algal oil, and rapeseed oil.

A modified natural oil, such as a partially hydrogenated vegetable oil or an oil modified by a fermentation process, can be used instead of or in combination with the natural oil. When a natural oil is partially hydrogenated or modified by fermentation, the site of unsaturation can migrate to a variety of positions on the hydrocarbon backbone of the fatty ester moiety. Because of this tendency, when the modified natural oil is self-metathesized or is cross-metathesized with the olefin, the reaction products will have a different and generally broader distribution compared with the product mixture generated from an unmodified natural oil. However, the products generated from the modified natural oil are similarly converted to inventive unsaturated alcohol derivative compositions. In certain embodiments, the naturally occurring oil may be refined, bleached, and/or deodorized.

The other reactant in the cross-metathesis reaction is an olefin. Suitable olefins are internal or α-olefins having one or more carbon-carbon double bonds. Mixtures of olefins can be used. Preferably, the olefin is a monounsaturated $C_2$-$C_{10}$ α-olefin, more preferably a monounsaturated $C_2$-$C_8$ α-olefin. Preferred olefins also include $C_4$-$C_9$ internal olefins. Thus, suitable olefins for use include, for example, ethylene, propylene, 1-butene, cis- and trans-2-butene, 1-pentene, isohexylene, 1-hexene, 3-hexene, 1-heptene, 1-octene, 1-nonene, 1-decene, and the like, and mixtures thereof.

Cross-metathesis is accomplished by reacting the natural oil and the olefin in the presence of a homogeneous or heterogeneous metathesis catalyst. The olefin is omitted when the natural oil is self-metathesized, but the same catalyst types are generally used. Suitable homogeneous metathesis catalysts include combinations of a transition metal halide or oxo-halide (e.g., $WOCl_4$ or $WCl_6$) with an alkylating cocatalyst (e.g., $Me_4Sn$). Preferred homogeneous catalysts are well-defined alkylidene (or carbene) complexes of transition metals, particularly Ru, Mo, or W. These include first and second-generation Grubbs catalysts, Grubbs-Hoveyda catalysts, and the like. Suitable alkylidene catalysts have the general structure:

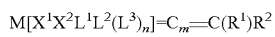

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086 ("the '086 publication"), the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is party of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

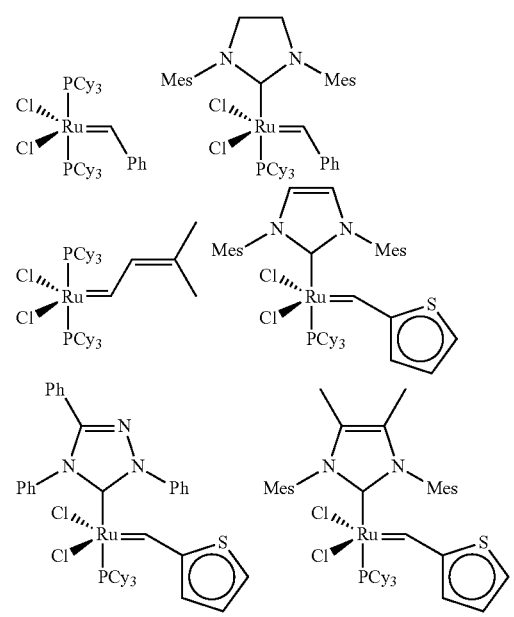

Heterogeneous catalysts suitable for use in the self- or cross-metathesis reaction include certain rhenium and molybdenum compounds as described, e.g., by J. C. Mol in *Green Chem.* 4 (2002) 5 at pp. 11-12. Particular examples are catalyst systems that include $Re_2O_7$ on alumina promoted by an alkylating cocatalyst such as a tetraalkyl tin lead, germanium, or silicon compound. Others include $MoCl_3$ or $MoCl_5$ on silica activated by tetraalkyltins.

For additional examples of suitable catalysts for self- or cross-metathesis, see U.S. Pat. No. 4,545,941, the teachings of which are incorporated herein by reference, and references cited therein. See also *J. Org. Chem.* 46 (1981) 1821; *J. Catal.* 30 (1973) 118; *Appl. Catal.* 70 (1991) 295; *Organometallics* 13 (1994) 635; *Olefin Metathesis and Metathesis Polymerization* by Ivin and Mol (1997), and *Chem. & Eng. News* 80(51), Dec. 23, 2002, p. 29, which also disclose useful metathesis catalysts. Illustrative examples of suitable catalysts include ruthenium and osmium carbene catalysts as disclosed in U.S. Pat. Nos. 5,312,940, 5,342,909, 5,710,298, 5,728,785, 5,728,917, 5,750,815, 5,831,108, 5,922,863, 6,306,988, 6,414,097, 6,696,597, 6,794,534, 7,102,047, 7,378,528, and U.S. Pat. Appl. Publ. No. 2009/0264672 A1, and PCT/US2008/009635, pp. 18-47, all of which are incorporated herein by reference. A number of metathesis catalysts that may be advantageously employed in metathesis reactions are manufactured and sold by Materia, Inc. (Pasadena, Calif.) and Evonik Degussa GmbH (Hanau, Germany).

The unsaturated fatty alcohols (also referred to hereinbelow as simply "unsaturated alcohols") are made by reacting a metathesis-derived monounsaturated alkyl ester, preferably a $C_5$-$C_{35}$ monounsaturated alkyl ester, and more preferably a $C_{10}$-$C_{17}$ monounsaturated lower alkyl ester, with a reducing agent. By "lower alkyl ester," we mean an ester derived from a $C_1$ to $C_{10}$ alcohol, preferably a $C_1$-$C_6$ alcohol, more preferably a $C_1$-$C_4$ alcohol, and most preferably methanol or ethanol. Thus, the lower alkyl ester is most preferably a methyl or ethyl ester. Suitable lower alkyl esters can be generated by transesterifying a metathesis-derived triglyceride. For example, cross-metathesis of a natural oil with an olefin, followed by removal of unsaturated hydrocarbon metathesis products by stripping, and then transesterification of the modified oil component with a lower alkanol under basic conditions provides a mixture of unsaturated lower alkyl esters. The unsaturated lower alkyl ester mixture can be purified to isolate particular alkyl esters prior to making the unsaturated alcohols and inventive derivatives.

Reduction of metathesis-derived monounsaturated alkyl esters to produce the unsaturated alcohols is performed using well-known catalysts and procedures. The reducing agent is typically either a hydride reducing agent (sodium borohydride, lithium aluminum hydride, or the like) or molecular hydrogen in combination with a metal catalyst, frequently copper and/or zinc in combination with chromium (see, e.g., U.S. Pat. Nos. 2,865,968; 3,193,586; 4,804,790; 5,124,491; 5,672,781; 6,683,224; 7,169,959 and 7,208,643, the teachings of which are incorporated herein by reference).

The skilled person will appreciate that the reduction process, particularly when transition metal catalysts are used to convert the lower alkyl esters to alcohols, can induce some degree of isomerization or migration of the carbon-carbon double bond from its original position. Moreover, because ester hydrogenation catalysts are not always completely selective, a proportion of the carbon-carbon double bonds might be hydrogenated during the ester reduction, resulting in a mixed product that may have saturated fatty alcohols in addition to the desired unsaturated fatty alcohols. The skilled person can control the degree of unsaturation to any desired amount.

General Note Regarding Chemical Structures:

As the skilled person will recognize, products made in accordance with the invention are typically mixtures of cis- and trans-isomers. Except as otherwise indicated, all of the structural representations provided herein show only a trans-isomer. The skilled person will understand that this convention is used for convenience only, and that a mixture of cis- and trans-isomers is understood unless the context dictates otherwise. Structures shown often refer to a principal product that may be accompanied by a lesser proportion of other components or positional isomers. For instance, sulfonation or sulfitation processes often give mixtures of sultones, alkanesulfonates, and alkenesulfonates, in addition to isomerized products. Thus, the structures provided represent likely or predominant products.

Some monounsaturated fatty alcohol compositions used to make the inventive derivatives have the general structure:

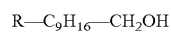

wherein R is H or $C_2$-$C_7$ alkyl. Preferably, the fatty alcohol compositions have the general structure:

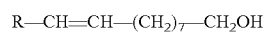

wherein R is H or $C_2$-$C_7$ alkyl.

Some specific examples of $C_{10}$, $C_{12}$, $C_{14}$, and $C_{16}$-based unsaturated alcohols used to make inventive derivatives appear below:

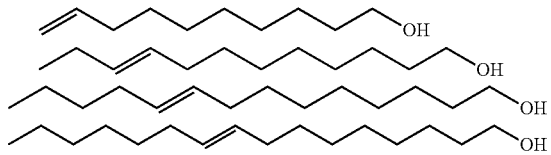

The inventive sulfate or sulfonate derivatives are made by one or more of alkoxylating, sulfating, sulfonating, and sulfitating the monounsaturated fatty alcohol compositions.

The unsaturated fatty alcohols can be alkoxylated, sulfated, or both using well-known techniques. For instance, the unsaturated fatty alcohol can be alkoxylated by reacting it with ethylene oxide, propylene oxide, or a combination thereof to produce an alkoxylate. Alkoxylations are usually catalyzed by a base (e.g., KOH), but other catalysts such as double metal cyanide complexes (see, e.g., U.S. Pat. No. 5,482,908) can also be used. The oxyalkylene units can be incorporated randomly or in blocks.

The unsaturated fatty alcohol can be sulfated, with or without a prior alkoxylation, and if applicable, neutralized to give a monounsaturated alkyl sulfate or a monounsaturated alkyl ether sulfate according to known methods (see, e.g., U.S. Pat. No. 3,544,613, the teachings of which are incorporated herein by reference). Sulfamic acid is a convenient reagent that sulfates the hydroxyl group without disturbing the unsaturation. Thus, warming the monounsaturated alcohol with sulfamic acid optionally in the presence of urea or another proton acceptor conveniently provides the desired monounsaturated alkyl ammonium sulfate (see examples below). The ammonium sulfate is easily converted to an alkali metal sulfate by reaction with an alkali metal hydroxide or other ion-exchange reagents. In the examples below, monounsaturated alkyl sodium sulfates are prepared from the corresponding ammonium sulfates by reacting the latter with aqueous sodium hydroxide.

Other reagents can be used to convert hydroxyl groups of an unsaturated alcohol or alkoxylate to sulfates. For instance, sulfur trioxide, oleum, or chlorosulfonic acid may be used. Some of these reagents can, under the right conditions, also react with the unsaturation to form a sulfonate (having a carbon-sulfur bond), which may or may not be the desired outcome. Sulfur trioxide, for instance, can be used to sulfate the hydroxyl group of an unsaturated alcohol or alkoxylate, but it may also react with a carbon-carbon double bond to generate a β-sultone, which can ring open to give mixtures of hydroxyalkane sulfonates and alkene sulfonates. Thus, it is possible, and may be desirable, to perform both sulfation and sulfonation in one pot, and often with a single reagent.

The unsaturated fatty alcohols or their derivatives can be sulfonated. Sulfonation is performed using well-known methods, including reacting the olefin with sulfur trioxide. Sulfonation may optionally be conducted using an inert solvent. Non-limiting examples of suitable solvents include liquid $SO_2$, hydrocarbons, and halogenated hydrocarbons. In one commercial approach, a falling film reactor is used to continuously sulfonate the olefin using sulfur trioxide. Other sulfonating agents can be used with or without use of a solvent (e.g., chlorosulfonic acid, fuming sulfuric acid), but sulfur trioxide is generally the most economical. The sultones that are the immediate products of reacting olefins with $SO_3$, chlorosulfonic acid, and the like may be subsequently subjected to a hydrolysis reaction with aqueous caustic to afford mixtures of alkene sulfonates and hydroxyalkane sulfonates. Suitable methods for sulfonating olefins are described in U.S. Pat. Nos. 3,169,142; 4,148,821; and U.S. Pat. Appl. Publ. No. 2010/0282467, the teachings of which are incorporated herein by reference.

Some processes are effective for both sulfonation (to form a carbon-sulfur bond) and sulfation (to form an oxygen-sulfur bond). A product having at least some proportion of material that is both sulfonated and sulfated might be desirable. For instance, a combined sulfate/sulfonate can impart beneficial properties to the bulk surfactant, including reduced viscosity, better concentratability, better compatibilizing properties, or other advantages.

Sulfonation might also be the preferred way to make a product that is only sulfonated despite the generation of both sulfonates and sulfates during the sulfonation process. In this case, the sulfate portion is readily converted back to an alcohol functionality by aqueous hydrolysis at relatively low or high pH without disturbing the sulfonate.

An exemplary product mixture that might be obtained by reacting 9-dodecen-1-ol with sulfur trioxide followed by neutralization and sultone hydrolysis appears below (note the possible sulfation of the hydroxyl group in addition to sulfonation at the carbon-carbon double bond):

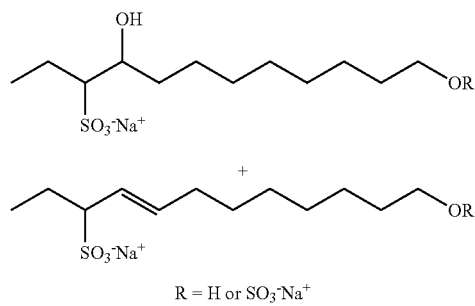

R = H or $SO_3^-Na^+$

The unsaturated fatty alcohols or their derivatives can be sulfitated. Sulfitation, a particular variety of sulfonation, is accomplished by combining the unsaturated alcohol or derivative in water (and usually a cosolvent such as isopropanol) with at least a molar equivalent of a sulfitating agent using well-known methods. Suitable sulfitating agents include, for example, sodium sulfite, sodium bisulfite, sodium metabisulfite, or the like. Optionally, a catalyst or initiator is included, such as peroxides, iron, or other free-radical initiators. Typically, the reaction mixture is conducted at 15-100° C. until the reaction is reasonably complete. Suitable methods for sulfitating olefins appear in U.S. Pat. Nos. 2,653,970; 4,087,457; 4,275,013, the teachings of which are incorporated herein by reference.

When an unsaturated fatty alcohol is the starting material, the derivative can comprise an alkyl sulfate, a sulfonated alkyl sulfate, an alcohol sulfonate, a sulfated alcohol sulfonate, or a mixture thereof. As used herein "alkyl" sulfates can be saturated or unsaturated.

The alkyl sulfates are made by reacting a monounsaturated fatty alcohol as described above with a sulfating agent to convert the alcohol functionality to a sulfate group ($OSO_3X$ in the examples below, where X is an alkali metal or ammonium). As the skilled person will recognize, hydration of the double bond to give an alcohol can sometimes occur under conditions used for sulfation. Examples of alkyl sulfates:

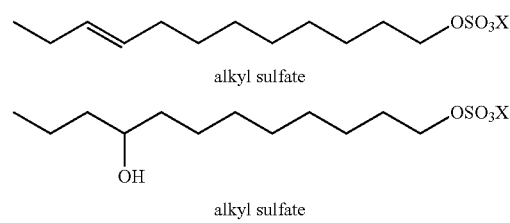

Some specific examples of $C_{10}$, $C_{12}$, $C_{14}$, and $C_{16}$-based alkyl sulfates:

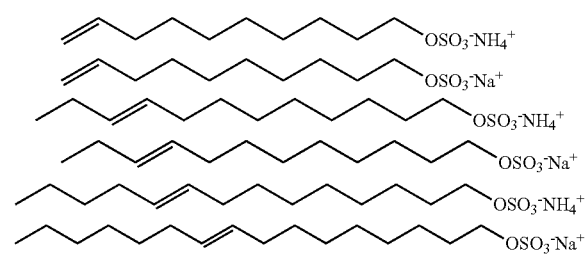

Because the alkyl sulfate can be hydrolyzed, preparation of hydroxyl-functional alkyl sulfates provides precursors to diols:

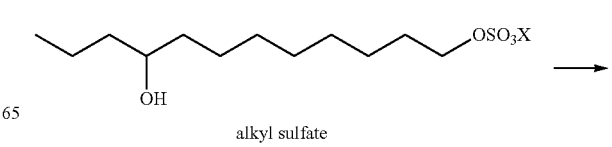

-continued

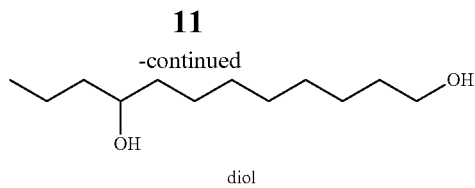

diol

The alkyl sulfate (which usually has monounsaturation) can be further reacted with a sulfitating agent (a particular kind of sulfonating agent) to give a sulfonated alkyl sulfate, which has at least one carbon-sulfur bond. One example of such a sulfonated alkyl sulfate:

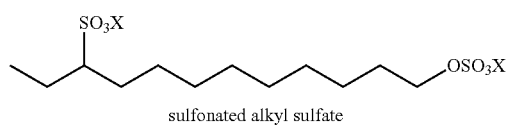

sulfonated alkyl sulfate

Alcohol sulfonates are made by reacting the unsaturated fatty alcohol with a sulfonating agent to form at least one carbon-sulfur bond. As shown in the examples below, the alcohol sulfonates might include saturated or unsaturated alcohols, disulfonated alcohols, or sulfonated diols:

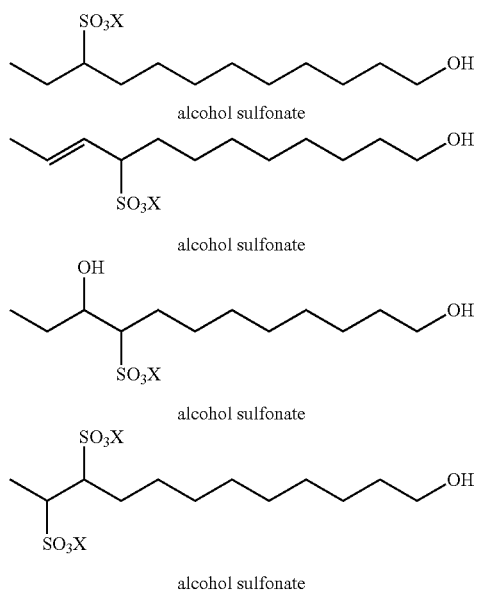

When the goal is to sulfonate the carbon-carbon double bond without also sulfating the alcohol, a "sulfitation" process is normally used. Sulfitation is described in more detail above. Some specific examples of alcohol sulfonates conveniently made by sulfitating $C_{10}$, $C_{12}$, $C_{14}$, and $C_{16}$-based alcohols appear below:

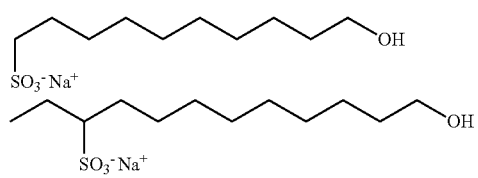

-continued

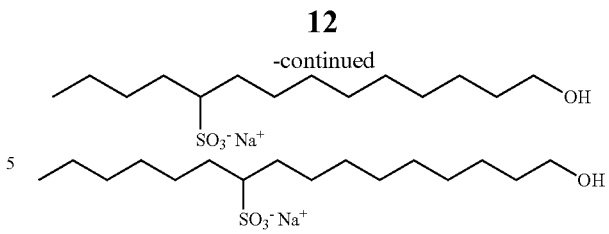

The alcohol sulfonate (which has hydroxyl functionality) can, if desired, be further reacted with a sulfating agent to give a sulfated alcohol sulfonate. Examples of sulfated alcohol sulfonates:

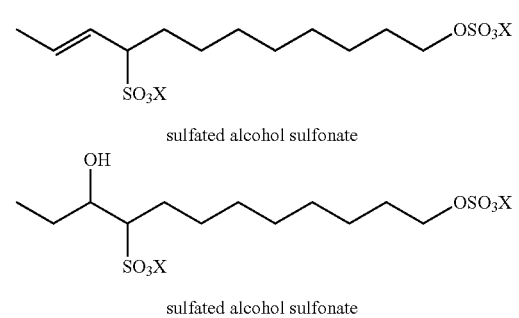

Depending on what conditions are used to sulfonate the monounsaturated fatty alcohol (discussed below), the product mixture can contain dialkylsulfates:

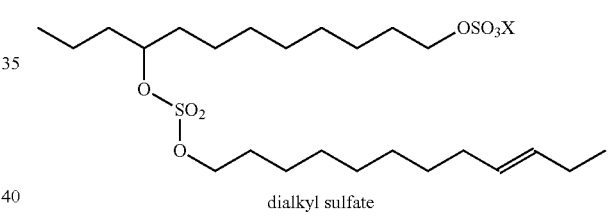

dialkyl sulfate

The invention includes unsaturated alkoxylates, preferably ethoxylates, made from the monounsaturated fatty alcohols.

Some specific examples of ethoxylates based on $C_{10}$, $C_{12}$, $C_{14}$, and $C_{16}$ unsaturated alcohols appear below:

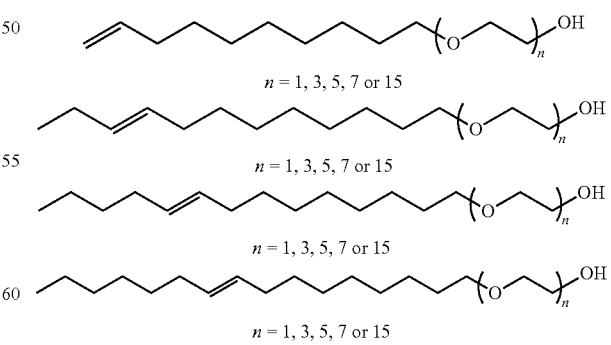

When an unsaturated fatty alcohol alkoxylate is the starting material, the derivative can comprise an ether sulfate, a sulfonated ether sulfate, an alkoxylate sulfonate, a sulfated alkoxylate sulfonate, or a mixture thereof.

The ether sulfates are made by reacting a monounsaturated fatty alcohol alkoxylate with a sulfating agent to convert the alcohol functionality to a sulfate group. Examples of ether sulfates:

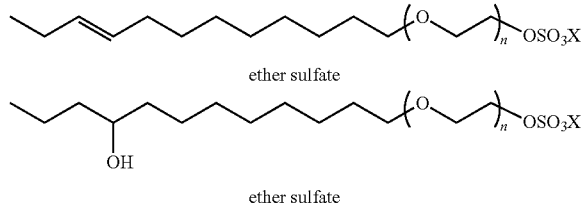

ether sulfate

Some specific examples of ether sulfates based on $C_{10}$ or $C_{12}$ unsaturated alcohols appear below:

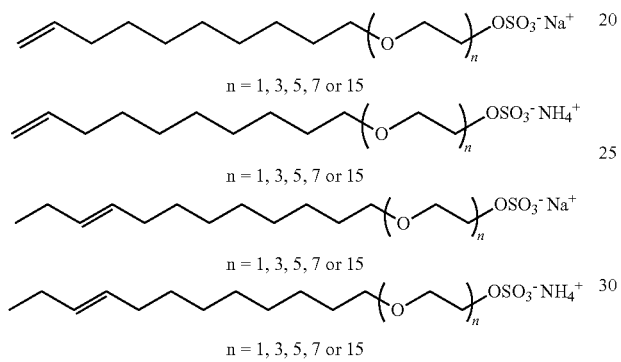

The ether sulfate (which usually has a monounsaturated component) can be further reacted with a sulfonating agent to give a sulfonated ether sulfate, which has at least one carbon-sulfur bond. One example of a sulfonated ether sulfate:

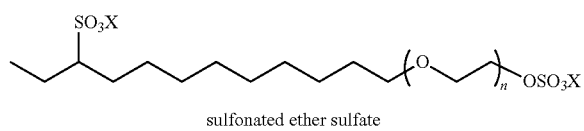

sulfonated ether sulfate

The alkoxylate sulfonates are made by reacting the unsaturated fatty alcohol alkoxylate with a sulfonating agent to form at least one carbon-sulfur bond. As shown in the examples below, the alkoxylate sulfonates might include saturated or unsaturated alcohols, disulfonated alcohols, or sulfonated diols:

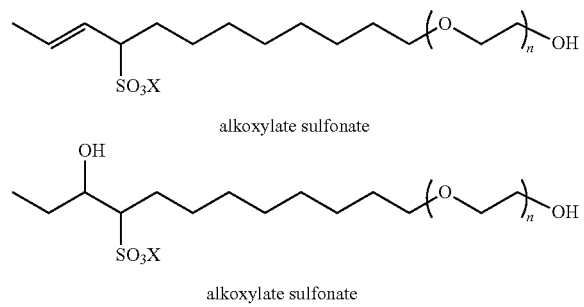

alkoxylate sulfonate

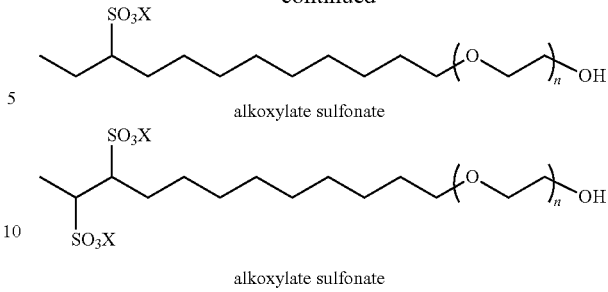

alkoxylate sulfonate

When the goal is to sulfonate the carbon-carbon double bond without also sulfating the alcohol, a "sulfitation" process is normally used. Sulfitation is described in more detail above. Some specific examples of sulfitated $C_{10}$ and $C_{12}$-based ethoxylates appear below:

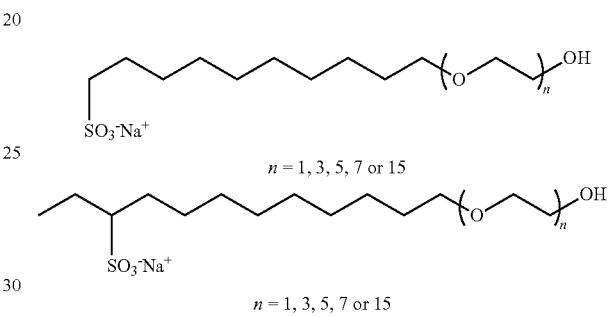

The alkoxylate sulfonate (which has hydroxyl functionality) can be further reacted with a sulfating agent to give a sulfated alkoxylate sulfonate. Examples of sulfated alkoxylate sulfonates:

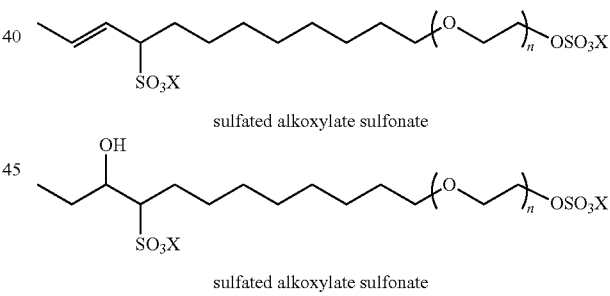

sulfated alkoxylate sulfonate

In one aspect, the sulfate or sulfonate derivative is prepared from a monounsaturated alkoxylate. The monounsaturated alkoxylate is made by reacting a monounsaturated alcohol (or alkoxide) with one or more alkylene oxides. As shown in the examples below, a series of products with different degrees of alkoxylation can be easily produced using a single reactor. This is illustrated by the sequential ethoxylation of 9-decen-1-ol or 9-dodecen-1-ol to produce ethoxylates having, on average, 1, 3, 5, 7, or 15 moles of oxyethylene units per mole of unsaturated fatty alcohol starter. (See, e.g., the preparation of ethoxylates from 9-decen-1-ol: A10-4, A10-7, A10-10, A10-13, and A10-16).

Thus, in one aspect, the alkoxylate is further reacted with a sulfating agent to give a monounsaturated alkyl ether sulfate. This is illustrated below in the conversion of the ethoxylates to the corresponding ether ammonium sulfates and ether sodium sulfates. Reaction of the ethoxylate with sulfamic acid in the presence of urea gives the corresponding alkyl ether ammonium sulfate, which can be reacted with sodium hydroxide to provide the corresponding alkyl ether sodium sulfate. See, e.g., the preparation of alkyl ether ammonium sulfates based on 9-docecen-1-ol shown below (A12-5, A12-8, A12-11, A12-14, and A12-17), and preparation of the corresponding alkyl ether sodium sulfates (A12-6, A12-9, A12-12, A12-15, and A12-18) from the ammonium sulfates.

In another aspect, the monounsaturated fatty alcohol is reacted directly with a sulfating agent to give a monounsaturated alkyl sulfate. In this simpler case, alkoxylation does not precede sulfation. This is illustrated below in the conversion of monounsaturated fatty alcohols to the corresponding alkyl ammonium sulfates and alkyl sodium sulfates. See, e.g., the preparation of ammonium sulfates (A10-2, A12-2) and sodium sulfates (A10-3, A12-3) based on 9-decen-1-ol or 9-dodecen-1-ol, respectively, which are shown below.

In one aspect, the derivative of the monounsaturated alcohol composition is a sulfate or ether sulfate having the general structure:

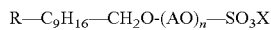

wherein R is H or $C_2$-$C_7$ alkyl; X is a mono- or divalent cation or an ammonium or substituted ammonium cation; AO is an oxyalkylene group; and n, which is the average number of oxyalkylene groups, has a value within the range of 0 to 200. Preferably, n has a value within the range of 0.1 to 100, preferably 1 to 50, more preferably 1 to 20. Preferably, the derivative has the general structure:

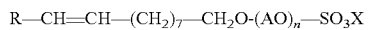

wherein R is H or $C_2$-$C_7$ alkyl; X is a mono- or divalent cation or an ammonium or substituted ammonium cation; AO is an oxyalkylene group; and n, which is the average number of oxyalkylene groups, has a value within the range of 0 to 200. Preferably, n has a value within the range of 0.1 to 100, preferably 1 to 50, more preferably 1 to 20.

In either of the above-mentioned general structures, AO can indicate a single kind of oxyalkylene group, blocks of different oxyalkylene groups, a random distribution of oxyalkylene groups (as in a random EO/PO copolymer), or any other distribution of oxyalkylene groups.

The invention includes a process for making sulfate or sulfonate derivatives. The process comprises first reducing a metathesis-derived monounsaturated alkyl ester, preferably a $C_5$-$C_{35}$ monounsaturated alkyl ester, and more preferably a $C_{10}$-$C_{17}$ monounsaturated lower alkyl ester, to produce a monounsaturated fatty alcohol composition. The fatty alcohol composition is then converted to a sulfate or sulfonate derivative by one or more of alkoxylating, sulfating, sulfonating, and sulfitating the monounsaturated fatty alcohol composition. Suitable reagents and processes for effecting the reduction have already been described. One suitable process comprises sulfating the monounsaturated alcohol composition to give an alkyl sulfate. Another suitable process comprises alkoxylating the fatty alcohol composition with one or more alkylene oxides, preferably ethylene oxide, to give a monounsaturated alkoxylate, followed by sulfation to give a monounsaturated alkyl ether sulfate. The process can also comprise sulfonating or sulfitating the monounsaturated fatty alcohol to give a sulfonate.

In one aspect, the invention relates to a sulfate composition. The composition comprises: (a) from 40 to 60 wt. % of a monounsaturated fatty primary alcohol sulfate; and (b) from 40 to 60 wt. % of a secondary hydroxyalkyl fatty primary alcohol sulfate. Preferably, the composition comprises 45 to 55 wt. % of the monounsaturated fatty primary alcohol sulfate; and from 45 to 55 wt. % of the secondary hydroxyalkyl fatty primary alcohol sulfate. The sulfate composition may further comprise 0.1 to 20 wt. %, preferably 0.5 to 15 wt. %, of sulfonated products.

Although sulfation and sulfonation are known to compete when an unsaturated fatty alcohol is the starting material, we surprisingly found that certain sulfation conditions, such as falling-film sulfation using sulfur trioxide, can provide roughly equal amounts of (a) a monounsaturated fatty primary alcohol sulfate and (b) a secondary hydroxyalkyl fatty primary alcohol sulfate. Without wishing to be bound to any particular theory, we believe that the products may result from formation of an intermediate dialkylsulfate. Upon neutralization of the acid, the dialkylsulfate may undergo both elimination, to revert back to the unsaturated alcohol sulfate, as well as hydrolysis to afford the hydroxyalkyl alcohol sulfate (see scheme below). The hydrolysis appears to be selective, providing preferentially the secondary alcohol and the primary alcohol sulfate. Consequently, the product mixture from reaction of a monounsaturated alcohol, particularly one that is not ethoxylated, typically comprises about 90% sulfates—with roughly equal amounts of monounsaturated primary alcohol sulfate and secondary hydroxyalkyl alcohol sulfate—and about 10% sulfonated products.

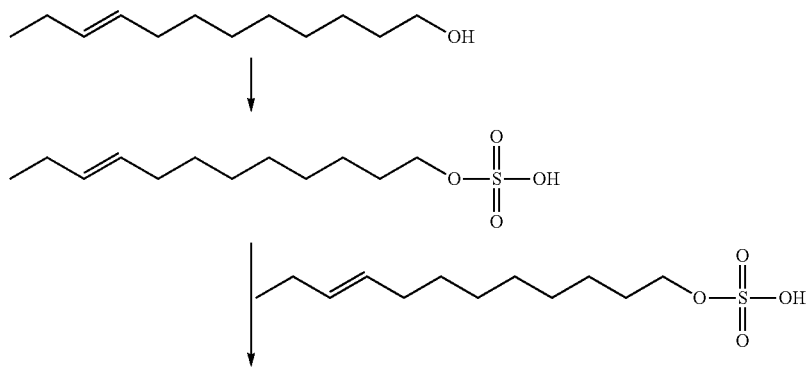

-continued

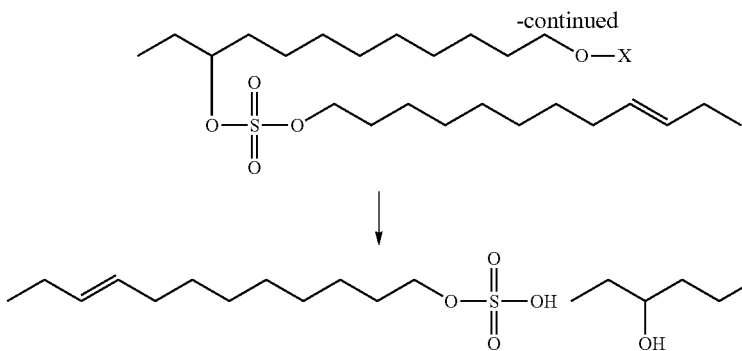

In contrast, when ethoxylated alcohols are subjected to falling-film sulfation with sulfur trioxide, the unsaturated ether sulfate predominates. For instance, an ethoxylate from 1 mole of EO gives about 65% unsaturated ether sulfate, and a 3 mole ethoxylate gives close to 90% unsaturated ether sulfate.

In a preferred aspect, the monounsaturated fatty primary alcohol sulfate and the secondary hydroxyalkyl fatty primary alcohol sulfate derive from a $C_8$-$C_{30}$ monounsaturated alcohol. More preferably, the two components of the sulfate composition derive from a $C_{10}$-$C_{17}$ monounsaturated alcohol. Preferably, the monounsaturated alcohol is metathesis-derived. An exemplary composition is A12-99, below.

In some preferred compositions, the monounsaturated fatty primary alcohol sulfate has the structure:

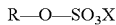

wherein R is a linear or branched $C_8$-$C_{30}$ monounsaturated hydrocarbyl group, X is a mono- or divalent cation or an ammonium or substituted ammonium cation. Preferably, R is a linear $C_{11}$-$C_{17}$ monounsaturated hydrocarbyl group.

We found that falling-film sulfation with sulfur trioxide tends to scramble carbon-carbon double bond geometry. Thus, the product mixture frequently approaches a thermodynamically preferred mixture of cis- and trans-isomers, usually about 8:2 trans-/cis-, even if the unsaturation in the unsaturated fatty alcohol was predominantly or exclusively cis- or trans-.

In other preferred aspects, the secondary hydroxyalkyl fatty primary alcohol sulfate has the structure:

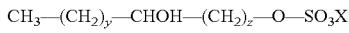

wherein y=0 to 28, z=0 to 28, y+z=6 to 28, X is a mono- or divalent cation or an ammonium or substituted ammonium cation. Preferably, y+z=9 to 15.

The sulfate compositions are preferably made by sulfating a monounsaturated fatty alcohol with sulfur trioxide in a falling-film reactor, followed by neutralization, according to methods described earlier.

We also found that terminal unsaturation is not retained when sulfur trioxide is used to make monounsaturated alcohol sulfates. Instead, isomerization occurs to give more-substituted unsaturated products. Thus, in one inventive process, an internally monounsaturated fatty alcohol sulfate is made. This process comprises reacting a terminally monounsaturated fatty alcohol with sulfur trioxide in a falling-film reactor, followed by neutralization. Preferably, the monounsaturated fatty alcohol is metathesis-derived.

We also observed positional isomerization upon sulfation of internally unsaturated alcohols. Again, without wishing to be bound by theory, this may occur through the regeneration of olefin when a dialkylsulfate eliminates in the "opposite" direction (or side of the chain) from which the addition had occurred. Thus, a 9-substituted dialkylsulfate could eliminate to give an 8-9 unsaturated product, and a 10-substituted dialkylsulfate could eliminate to a 10-11 unsaturated product. Whether or not the olefin can fully "zip" up and down the chain is unclear, but our observation of an 11-hydroxy-substituted C12 alkyl sulfate suggests either a multiple addition/elimination "cycling" phenomenon or that olefin can migrate prior to addition of sulfuric acid ester.

The invention provides compositions comprising at least one sulfate or sulfonate derivative or sulfate composition. The composition may be an aqueous system or provided in other forms. The sulfate or sulfonate derivatives and compositions may be incorporated into various formulations and used as surfactants, emulsifiers, skin feel agents, film formers, rheological modifiers, solvents, release agents, biocides, biocide potentiators, conditioners, dispersants, hydrotropes, or the like. Such formulations may be used in end-use applications including, among others: personal care; household, industrial, and institutional cleaning products; oil field applications; enhanced oil recovery; gypsum foamers; coatings, adhesives and sealants; and agricultural formulations.

Thus, the sulfate or sulfonate derivatives and compositions may be used in such personal care applications as bar soaps, bubble baths, liquid cleansing products, conditioning bars, oral care products, shampoos, body washes, facial cleansers, hand soaps/washes, shower gels, wipes, baby cleansing products, creams/lotions, hair treatment products, antiperspirants, and deodorants.

Cleaning applications include, among others, household cleaners, degreasers, sanitizers and disinfectants, liquid and powdered laundry detergents, heavy duty liquid detergents, light-duty liquid detergents, hard and soft surface cleaners for household, autodish detergents, rinse aids, laundry additives, carpet cleaners, spot treatments, softergents, liquid and sheet fabric softeners, industrial and institutional cleaners and degreasers, oven cleaners, car washes, transportation cleaners, drain cleaners, industrial cleaners, foamers, defoamers, institutional cleaners, janitorial cleaners, glass cleaners, graffiti removers, concrete cleaners, metal/machine parts cleaners, and food service cleaners.

In specialty foam applications (firefighting, gypsum, concrete, cement wallboard), the sulfate or sulfonate derivatives and compositions function as foamers, wetting agents, and foam control agents.

In paints and coatings, the sulfate or sulfonate derivatives and compositions are used as solvents, coalescing agents, or additives for emulsion polymerization.

In oil field applications, the sulfate or sulfonate derivatives and compositions can be used for oil and gas transport, production, stimulation, enhanced oil recovery, and as components of drilling fluids.

In agricultural applications, the sulfate or sulfonate derivatives and compositions are used as solvents, dispersants, surfactants, emulsifiers, wetting agents, formulation inerts, or adjuvants.

As demonstrated in the examples below, the inventive sulfate or sulfonate derivatives and compositions are exceptionally useful as agricultural dispersants, surfactants for water-soluble herbicides, anionic emulsifiers for agricultural use, hard surface cleaners, foam control agents in gypsum applications, and primary surfactants for personal cleansers.

The following examples merely illustrate the invention. The skilled person will recognize many variations that are within the spirit of the invention and scope of the claims.

Reduction of Methyl 9-Decenoate to 9-Decen-1-ol (A10-1)

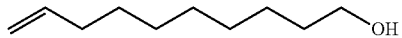

The procedure of Micovic and Mihailovic (*J. Org. Chem.* 18 (1953) 1190) is generally followed. Thus, a 5-L flask equipped with a mechanical stirrer, thermocouple, addition funnel, and nitrogen inlet is charged with tetrahydrofuran ("THF," 3 L). The flask is immersed in an isopropanol/$CO_2$ bath. Lithium aluminum anhydride (LAH) pellets (133.8 g) are charged to the flask with stirring. Methyl 9-decenoate (250 g) is charged to the addition funnel and diluted with THF to the maximum capacity of the funnel (500 mL). The ester solution is added dropwise to the LAH suspension at a rate that maintains the reaction temperature below 20° C. The funnel is refilled with pure ester (750 g; total of 1000 g) due to the large volume of the reaction mixture, and the addition continues. Total addition time of the ester: 5 h. Once the addition is complete, the reaction temperature is ~15° C. and stirring continues for 30 min. $^1$H NMR analysis shows complete conversion of the ester to the desired alcohol.

Deionized water (135 g) is added slowly via the addition funnel while keeping the temperature below 20° C. Hydrogen evolution appears to cease after approximately half of the water is added. The viscosity of the mixture increases, but it remains stirrable. The flask is removed from the cooling bath, and aqueous sodium hydroxide (15% aq. NaOH, 135 g) is added. During this addition, the reaction mixture thickens and quickly becomes an unstirrable slurry that has to be broken up with a spatula. Addition of the remaining NaOH solution proceeds without incident. Following the 15% NaOH addition, deionized water (3×135 g) is added. The slurry stirs for 20 min. and then stands overnight at room temperature. The mixture is filtered through a Buchner funnel, and the filter cake is washed with additional THF (2×500 mL) and then acetone (2×500 mL). The filtrates are combined and concentrated. $^1$H NMR analysis of the remaining oil reveals a clean alcohol product. The crude alcohol is transferred to a round-bottom flask and heated to 50° C. Full vacuum is slowly applied to remove low-boiling volatiles. The remaining crude product is then vacuum distilled, collecting the product that boils at 95-98° C. (97.5-100° C. pot temperature). Yield of A10-1: 834.7 g (98.3%). Purity (by GC analysis): 99.7%. Hydroxyl value: 355.5 mg KOH/g sample; iodine value: 162.2 g $I_2$/100 g sample. $^1$H NMR ($\delta$, $CDCl_3$): 5.8 ($CH_2$=CH—); 4.95 ($CH_2$=CH—); 3.6 (—$CH_2$—OH). The procedure is repeated four times using 1 kg of ester in each reduction.

C10 Alcohol Ammonium Sulfate, A10-2

A resin kettle equipped with a mechanical stirrer, thermocouple, temperature controller, heating mantle, and nitrogen inlet is charged with 9-decen-1-ol ("A10-1," 400 g), sulfamic acid (256.0 g), and urea (3.94 g). The mixture is heated with strong agitation to 105° C. and maintained for 6 h. $^1$H NMR analysis of the material upon cooling indicates 75% conversion of alcohol. The solid mass is transferred to an Erlenmeyer flask and chloroform (2 L) is added. Upon heating to boiling, product and unreacted alcohol dissolve, while unreacted sulfamic acid and urea solids settle from the mixture. The turbid, upper liquid layer is decanted from the solids and allowed to cool overnight to allow the product to recrystallize. The recrystallized solids are isolated by vacuum filtration, washed with cold $CHCl_3$ (1 L), air dried, and then dried under vacuum to constant mass. Half of the product is set aside to be used in the preparation of sample A10-3. $^1$H NMR on alkyl ammonium sulfate A10-2 is run in triplicate, twice in MeOD and once in $D_2O$, and the amount of unsulfated alcohol relative to actives is calculated from the results. Anionic actives: 96.3%; free alcohol: 1.95%; inorganic sulfates: 0.38%. $^1$H NMR ($\delta$, $d_4$-MeOH): 5.8 ($CH_2$=CH—); 4.9 ($CH_2$=CH—); 3.95 (—$CH_2$—OS(O)$_2$ONH$_4$).

C10 Alcohol Sodium Sulfate, A10-3

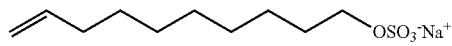

Alkyl ammonium sulfate A10-2 (230.5 g) and methanol (1 L) are charged to a flask, and the solution is warmed gently to 30° C. Sodium hydroxide (50% aq. solution, 72.8 g) is added slowly, maintaining the temperature below 35° C. and monitoring pH. Final pH is 10.5. The mixture is concentrated to a wet paste by rotary evaporation using a 50° C. water bath. The semi-solid product is then transferred to a dish and dried thoroughly in a 70° C. vacuum oven, occasionally mixing and breaking up solids, for 4 h. The alkyl sodium sulfate, A10-3, is obtained as a white powder. Yield: 227.5 g (97%). Anionic actives: 97.4%; free alcohol ($^1$H NMR): 0.73%; inorganic sulfates: 0.36%. $^1$H NMR: (6, $d_4$-MeOH): 5.7 ($CH_2$=CH—); 4.8 ($CH_2$=CH—); 3.88 (—$CH_2$—OS(O)$_2$ONa).

Reduction of Methyl 9-Dodecenoate to 9-Dodecen-1-ol (A12-1)

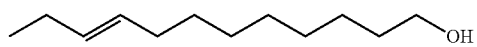

The procedure used to prepare A10-1 is generally followed using THF (3 L), lithium aluminum hydride pellets (116 g), and methyl 9-dodecenoate (1000 g total).

The usual work-up follows, first with deionized water (120 g), then aqueous sodium hydroxide (15% aq. NaOH, 120 g). Following the 15% NaOH addition, deionized water (360 g) is added. The slurry stirs for 20 min. and then stands overnight at room temperature. The mixture is filtered through a Buchner funnel, and the filter cake is washed with additional THF (4×1 L). The filtrates are combined and concentrated.

The procedure is repeated five times using 1 kg of methyl 9-dodecenoate for each run, and the crude alcohol products are combined and distilled as described above for the preparation of A10-1. Yield of A12-1: 4262.8 g (98.2%). Purity (by GC analysis): 99.4%. Hydroxyl value: 302.8 mg KOH/g sample; iodine value: 133.2 g $I_2$/100 g sample. $^1$H NMR ($\delta$, CDCl$_3$): 5.4 (—CH=CH—); 3.6 (—CH$_2$—OH); 0.9 (CH$_3$—).

C12 Alcohol Ammonium Sulfate, A12-2

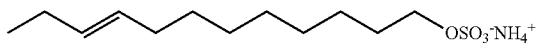

9-Dodecen-1-ol ("A12-1," 395.8 g), sulfamic acid (214.7 g) and urea (3.7 g) are charged to a resin kettle equipped as described for the preparation of A10-2. The mixture is slowly heated to 105° C. and stirs with vigorous agitation for 7 h. $^1$H NMR shows 75% conversion to sulfate. The resulting mass is broken up and transferred to an Erlenmeyer flask. Approximately 3 L of petroleum ether is added and the mixture is warmed with stirring to give a milky solution. The liquid portion is decanted away from insoluble salts, and this gives a precipitate upon cooling. The mixture is filtered with a Buchner funnel, and the filter cake is stripped in a Büchi beaker flask at 40° C. to recover the alkyl ammonium sulfate product, A12-2 (326.1 g). Purity (by $^1$H NMR): 97%. A portion (163.9 g) is reserved for use in preparing A12-3. Free alcohol ($^1$H NMR): 2.12 wt. %. $^1$H NMR ($\delta$, d$_4$MeOH): 5.4 (—CH=CH—); 3.88 (—CH$_2$—OS(O)$_2$ONH$_4$); 0.9 (CH$_3$—).

C12 Alcohol Sodium Sulfate, A12-3

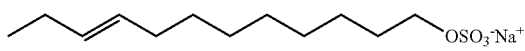

Alkyl ammonium sulfate A12-2 (163.9 g), and methanol (1 L) are charged to a round-bottom flask equipped with magnetic stirring and temperature controller. The mixture is heated to 30° C. resulting in a hazy solution. Sodium hydroxide (50% aq. solution, 46.6 g) is slowly added with a nitrogen sparge to aid removal of ammonia. The pH remains ~10 throughout the addition of caustic. Thereafter, the contents are transferred to a Büchi beaker flask. Methanol, water, and ammonia are stripped at 40° C., then up to 60° C. The solids are dried under high vacuum to give the desired alkyl sodium sulfate, A12-3 (165.3 g). Purity (by $^1$H NMR): 97%; free alcohol ($^1$H NMR): 2.14 wt. %. $^1$H NMR ($\delta$, d$_4$-MeOH): 5.4 (—CH=CH); 3.98 (—CH$_2$—OS(O)$_2$ONa); 0.9 (CH$_3$—).

The procedure used to make A12-3 is generally followed starting with 9-tetradecen-1-ol to produce A14-2, a C14 alcohol sodium sulfate:

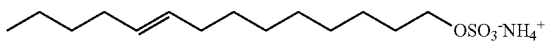

Ethoxylation of 9-Decen-1-Ol to Produce 1, 3, 5, 7, and 15 Mole Alcohol Ethoxylates (A10-4, A10-7, A10-10, A10-13, and A10-16, Respectively)

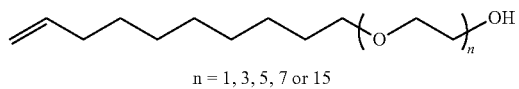

n = 1, 3, 5, 7 or 15

Ethoxylations are performed sequentially using one reactor to prepare unsaturated alcohol ethoxylates from 9-decen-1-ol that have, on average, 1, 3, 5, 7, or oxyethylene units.

9-Decen-1-ol (3417.8 g) is charged to a 2.5-L pressure reactor. Liquid KOH (45%, 45.0 g) is added. The reactor is sealed and heated to 75° C. under nitrogen with agitation. At ~75° C., vacuum is applied to remove water. The contents are further heated to 105-115° C. under full vacuum and held for 4 h with a nitrogen sparge. Vacuum is released, and a removed sample has a water content of 0.04%.

The remaining dried catalyzed alcohol feed (3332.0 g) is heated to 145° C. The reactor is pressurized with nitrogen and vented three times. Ethylene oxide (925 g, 1 mole per mole of starter) is introduced to the reactor at 145-160° C. After the EO addition, the mixture digests for 1 h at 150-160° C. until the reactor pressure equilibrates. The mixture is cooled to 60° C. and partially drained (1175.0 g removed) to provide the 1 mole ethoxylated unsaturated alcohol, A10-4. Hydroxyl value: 281.3 mg KOH/g; iodine value: 125.4 g $I_2$/100 g sample; polyethylene glycol: 0.13%. $^1$H NMR ($\delta$, d$_4$-MeOH): 5.8 (CH$_2$=CH—); 4.9 (CH$_2$=CH—); 3.65-3.45 (—CH$_2$—CH$_2$—OH).

The reactor contents (3082.0 g) are re-heated to 150° C., and the reactor is vented with nitrogen as described earlier. Ethylene oxide (1340.0 g, 2 additional moles per mole of starter; 3 moles of EO per mole of 9-decen-1-ol charged) is added to the feed at 145-160° C. After digesting 1 h at 150-160° C., the mixture is cooled to 60° C. and partially drained (1233.3 g removed) to recover the 3 mole ethoxylated unsaturated alcohol, A10-7. Hydroxyl value: 194.2 mg KOH/g; iodine value: 86.5 g $I_2$/100 g sample; polyethylene glycol: 0.24%. $^1$H NMR ($\delta$, d$_4$-MeOH): 5.8 (CH$_2$=CH—); 4.9 (CH$_2$=CH—); 3.65-3.45 (—CH$_2$—CH$_2$—O—).

The reactor contents (3188.7 g) are re-heated to 150° C. as described above. Ethylene oxide (970 g, 2 additional moles per mole of starter; 5 moles of EO per mole of 9-decen-1-ol charged) is added to the feed at 145-160° C. After digesting 1 h at 150-160° C., the mixture is cooled to 60° C. and partially drained (1277.8 g removed) to recover the 5 mole ethoxylated unsaturated alcohol, A10-10. Hydroxyl value: 146.5 mg KOH/g; iodine value: 65.8 g $I_2$/100 g sample; polyethylene glycol: 0.29%. $^1$H NMR ($\delta$, d$_4$-MeOH): 5.8 (CH$_2$=CH—); 4.9 (CH$_2$=CH—); 3.65-3.45 (—CH$_2$—CH$_2$—O—).

The reactor contents (2880.8 g) are re-heated to 150° C. as described above. Ethylene oxide (670 g, 2 additional moles per mole of starter; 7 moles of EO per mole of 9-decen-1-ol charged) is added to the feed at 145-160° C. After digesting 1 h at 150-160° C., the mixture is cooled to 60° C. and partially drained (1301.1 g removed) to recover the 7 mole ethoxylated unsaturated alcohol, A10-13. Hydroxyl value: 118.5 mg KOH/g; iodine value: 53.0 g $I_2$/100 g sample; polyethylene glycol: 0.27%. $^1$H NMR ($\delta$, d$_4$-MeOH): 5.8 (CH$_2$=CH—); 4.9 (CH$_2$=CH—); 3.65-3.45 (—CH$_2$—CH$_2$—O—).

The reactor contents (2249.7 g) are re-heated to 150° C. Ethylene oxide (1695 g, 8 additional moles per mole of starter; 15 moles of EO per mole of 9-decen-1-ol charged) is added at 145-160° C. After digesting 1 h at 150-160° C., the mixture is cooled to 60° C. and drained to provide the 15 mole ethoxylated unsaturated alcohol, A10-16 (3944.8 g). Hydroxyl value: 67.8 mg KOH/g; iodine value: 30.1 g $I_2$/100 g sample; polyethylene glycol: 1.18%. $^1$H NMR ($\delta$, $d_4$-MeOH): 5.8 (CH$_2$=CH—); 4.9 (CH$_2$=CH—); 3.65-3.45 (—CH$_2$—CH$_2$—O—).

1 Mole Ethoxylated C10 Alcohol, Ammonium Sulfate, A10-5

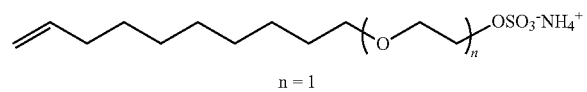

n = 1

Ethoxylated alcohol A10-4 (360 g), sulfamic acid (183.7 g), and urea (6.52 g) are charged to a round-bottom flask equipped with a mechanical stirrer, thermocouple, nitrogen inlet, and condenser. The mixture is heated to 100° C. with vigorous stirring and held for 4 h. $^1$H NMR shows a complete reaction. The mixture is cooled to 60° C. and diluted with chloroform (800 mL). Undissolved solids are removed, and the filtrate is concentrated as much as possible on a rotary evaporator. The resulting pasty solids are transferred to a baking dish and dried in a vacuum oven at 60° C. for 86 h. Yield of ether ammonium sulfate A10-5: 490 g.

1 Mole Ethoxylated C10 Alcohol, Sodium Sulfate, A10-6

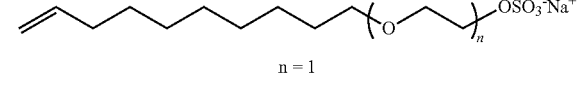

n = 1

Ether ammonium sulfate A10-5 (250 g, 0.84 mol) is charged to a round-bottom flask and diluted with methanol (500 g). Sodium methoxide (151.4 g of a 30 wt. % solution in methanol, 0.84 mol of CH$_3$ONa) is added slowly, and the solution is mixed thoroughly. The reaction mixture is heated to 40° C. and held for 30 min. $^1$H NMR indicates a complete reaction. The mixture is concentrated at 40° C., then at 50° C. The residue is transferred to a glass baking dish and dried in a vacuum oven (8 h, 60° C.) to give ether sodium sulfate A10-6 as a tan solid. Yield: 240 g.

3 Mole Ethoxylated C10 Alcohol, Ammonium Sulfate, A10-8

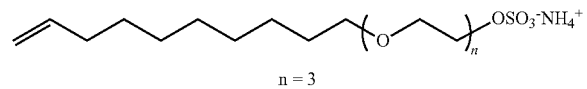

n = 3

Ethoxylated alcohol A10-7 (372 g, 1.29 mol) is charged to a round-bottom flask equipped with a mechanical stirrer, thermocouple, and nitrogen inlet. Sulfamic acid (129 g, 1.33 mol, 1.03 equiv) is added to the stirred material under nitrogen. The mixture is heated to 105° C. with vigorous stirring, and sulfamic acid slowly dissolves during the reaction. After 5 h at 105° C., the mixture cools to room temperature under nitrogen. The product, a viscous paste at room temperature, is shown by $^1$H NMR to be mostly the desired ammonium sulfate. The initial pH of 3.3 (10% aqueous) is adjusted to 7.38 using NH$_4$OH at 50° C. Yield of ether ammonium sulfate A10-8: 497.2 g. A portion (247.2 g) is set aside for conversion to the Na salt (A10-9). $^1$H NMR ($\delta$, $d_4$-MeOH): 5.8 (CH$_2$=CH—); 4.9 (CH$_2$=CH—); 4.1 (—O—CH$_2$—CH$_2$—OS(O)$_2$ONH$_4$).

3 Mole Ethoxylated C10 Alcohol, Sodium Sulfate, A10-9

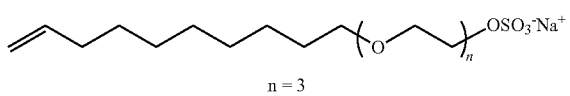

n = 3

Ether ammonium sulfate A10-8 (247.2 g) is diluted with methanol (~750 mL) and the mixture is warmed to 35° C. Sodium hydroxide solution (51.5 g of 50% aq. NaOH) is added dropwise over ~1 h. When the addition is complete, stirring continues for ~30 min, and the mixture then cools to room temperature. A fine white precipitate (Na$_2$SO$_4$) is removed, and the solid is rinsed with additional methanol. The clear yellow filtrate is concentrated to dryness on a rotary evaporator. Foaming becomes problematic at end of stripping, and drying is completed under high vacuum. The material is warmed with a heat gun to partially melt/fluidize it, and full vacuum is applied to give a semi-flocculent, waxy paste. A small aliquot is dried under high vacuum for $^1$H NMR analysis, and its spectrum is consistent with the desired product. The bulk product, ether sodium sulfate A10-9, is dried overnight under full vacuum to give a waxy paste (254.8 g).

5 Mole Ethoxylated C10 Alcohol, Ammonium Sulfate, A10-11

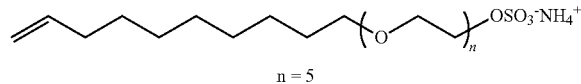

n = 5

Ethoxylated alcohol A10-10 (120 g, 0.32 mol) is charged to a round-bottom flask equipped with a mechanical stirrer, thermocouple, and nitrogen inlet. Sulfamic acid (32 g, 0.33 mol, 1.03 equiv) is added to the stirred material under nitrogen. The mixture is heated to 100° C. and held ~4 h with vigorous stirring. Sulfamic acid slowly dissolves during the reaction. $^1$H NMR analysis after 4 h indicates a complete reaction. The mixture is cooled to 50° C., and the pH is adjusted with NH$_4$OH via pipette. Initial pH (at 10% aq.): 2.85; final pH: 7.5. Yield of ether ammonium sulfate A10-11: 148.7 g. Free alcohol ($^1$H NMR): 1.6 wt. %. $^1$H NMR ($\delta$, $d_a$-MeOH): 5.8 (CH$_2$=CH—); 4.9 (CH$_2$=CH—); 4.1 (—O—CH$_2$—CH$_2$—OS(O)$_2$ONH$_4$).

5 Mole Ethoxylated C10 Alcohol, Sodium Sulfate, A10-12

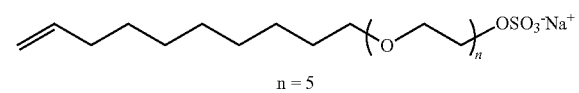

n = 5

Ether ammonium sulfate A10-11 (338.1 g) is diluted with methanol (1500 mL) in a round-bottom flask, and the mixture is warmed to 35° C. Sodium hydroxide (56.9 g of 50% aq. NaOH) is added slowly with stirring. When the addition is complete, a fine white precipitate (Na$_2$SO$_4$) is removed, and the solid is rinsed with additional methanol. The filtrate is concentrated to give ether sodium sulfate A10-12. Free alcohol: 1.42%. $^1$H NMR ($\delta$, $d_4$-MeOH): 5.8 (CH$_2$=CH—); 4.9 (CH$_2$=CH—); 4.1 (—O—CH$_2$—CH$_2$—OS(O)$_2$ONa).

7 Mole Ethoxylated C10 Alcohol, Ammonium Sulfate, A10-14

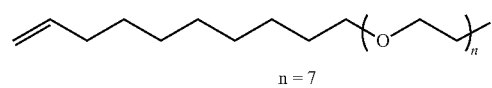

n = 7

Ethoxylated alcohol A10-13 (412 g, 0.89 mol) is charged to a round-bottom flask equipped with a mechanical stirrer, thermocouple, and nitrogen inlet. Sulfamic acid (88.7 g, 0.91 mol, 1.03 equiv) is added to the stirred material under nitrogen. The mixture is heated to 105° C. and held ~3 h, and sulfamic acid slowly dissolves during the reaction. After 3 h at 105° C., the mixture cools to room temperature under nitrogen. The viscous liquid is reheated to 50° C. for pH adjustment using aqueous NH$_4$OH. Initial pH: 3.3 (10% aqueous); final pH: 7.6. Yield of ether ammonium sulfate A10-14: 500.7 g. Half of this product is converted to the corresponding Na salt (A10-15). Free alcohol (by $^1$H NMR): not detected. $^1$H NMR (5, CDCl$_3$): 5.8 (CH$_2$=CH—); 4.9 (CH$_2$=CH—); 4.2 (—O—CH$_2$—CH$_2$—OS(O)$_2$ONH$_4$).

7 Mole Ethoxylated C10 Alcohol, Sodium Sulfate, A10-15

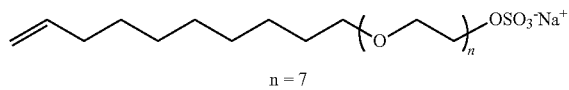

n = 7

Ether ammonium sulfate A10-14 (250.7 g) is diluted with methanol (~750 mL), and the mixture is warmed to 35° C. Sodium hydroxide (37 g of 50% aq. NaOH) is added dropwise over ~1 h. When the addition is complete, stirring continues for ~30 min and then the mixture is cooled to room temperature. A fine white precipitate (Na$_2$SO$_4$) is removed by filtration, and the solid is rinsed with additional methanol. The clear yellow filtrate is concentrated on a rotary evaporator. Foaming becomes problematic, and drying is completed under high vacuum. The material is warmed with a heat gun to partially fluidize it, and full vacuum is applied until evolution of volatiles ceases. A small aliquot is dried under high vacuum for $^1$H NMR analysis, and it gives a spectrum consistent with the desired product. The dried alcohol sodium sulfate, A10-15, is a thick syrup at room temperature. Yield: 247.8 g. Free alcohol (by $^1$H NMR): not detected. $^1$H NMR (5, CDCl$_3$): 5.7 (CH$_2$=CH—); 4.9 (CH$_2$=CH—); 4.1 (—O—CH$_2$—CH$_2$—OS(O)$_2$ONa).

15 Mole Ethoxylated C10 Alcohol, Ammonium Sulfate, A10-17

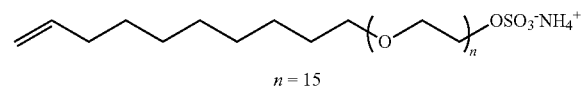

n = 15

A kettle equipped with a mechanical stirrer, thermocouple, temperature controller, heating mantle, nitrogen inlet, and condenser is charged with molten ethoxylated alcohol A10-16 (445.8 g) and sulfamic acid (53.9 g). The mixture is heated with strong agitation to 105° C. and held for 2 h. $^1$H NMR analysis indicates a complete reaction. The mixture is cooled to 60° C., and the pH is adjusted to neutral with ammonium hydroxide (10% aq. solution). Yield of ether ammonium sulfate A10-17: 488 g. Free alcohol (by $^1$H NMR): not detected. $^1$H NMR (δ, d$_4$-MeOH): 5.8 (CH$_2$=CH—); 5.0 (CH$_2$=CH—); 4.1 (—O—CH$_2$—CH$_2$—OS(O)$_2$ONH$_4$).

15 Mole Ethoxylated C10 Alcohol, Sodium Sulfate, A10-18

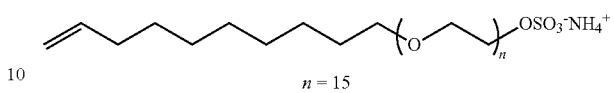

n = 15

Ether ammonium sulfate A10-17 (237 g) and methanol (1.5 L) are charged to a round-bottom flask. The solution is warmed to 35° C., and sodium hydroxide (20.5 g of 50% aq. NaOH) is added dropwise. After the addition is complete, the material is concentrated on a rotary evaporator, then dried under vacuum for 4 h. Yield of alcohol sodium sulfate A10-18: 231 g. Free alcohol (by $^1$H NMR): not detected. $^1$H NMR (δ, d$_4$-MeOH): 5.8 (CH$_2$=CH—); 4.9 (CH$_2$=CH—); 4.1 (—O—CH$_2$—CH$_2$—OS(O)$_2$ONa).

Ethoxylation of 9-Dodecen-1-Ol to Produce 1, 3, 5, 7, and 15 Mole Alcohol Ethoxylates (A12-4, A12-7, A12-10, A12-13, and A12-16, Respectively)

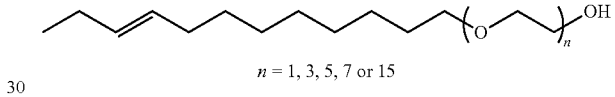

n = 1, 3, 5, 7 or 15

Ethoxylations are performed sequentially using one reactor to prepare unsaturated alcohol ethoxylates from 9-dodecen-1-ol that have, on average, 1, 3, 5, 7, or 15 oxyethylene units.

The procedure used to make the corresponding products from 9-decen-1-ol is generally followed. Thus, 9-dodecen-1-ol (3682.6 g) is charged to a 2.5-L pressure reactor. Liquid KOH (45%, 34.0 g) is added. The reactor is sealed and heated to 100° C. under nitrogen with agitation. At ~100° C., vacuum is applied to remove water. The contents are further heated to 115° C. under full vacuum and held for 3 h with a nitrogen sparge. Vacuum is released, and a removed sample has a water content of 0.03%.

The remaining dried catalyzed alcohol feed (3584.5 g) is heated to 145° C. The reactor is pressurized with nitrogen and vented three times. Ethylene oxide (850 g, 1 mole per mole of starter) is introduced to the reactor at 145-160° C. After the EO addition, the mixture digests for 1 h at 150-160° C. until the reactor pressure equilibrates. The mixture is cooled to 60° C. and partially drained (1167.0 g removed) to provide the 1 mole ethoxylated unsaturated alcohol, A12-4. Hydroxyl value: 246.4 mg KOH/g; iodine value: 106.8 g I$_2$/100 g sample; polyethylene glycol: 0.26%. $^1$H NMR (δ, CDCl$_3$): 5.3 (—CH=CH—); 3.7-3.4 (—CH$_2$—CH$_2$—O—); 0.9 (CH$_3$—).

The reactor contents (3267.8 g) are re-heated to 150° C., and the reactor is vented with nitrogen as described earlier. Ethylene oxide (1250 g, 2 additional moles per mole of starter; 3 moles of EO per mole of 9-dodecen-1-ol charged) is added to the feed at 145-160° C. After digesting 1 h at 150-160° C., the mixture is cooled to 60° C. and partially drained (1219.8 g removed) to recover the 3 mole ethoxylated unsaturated alcohol, A12-7. Hydroxyl value: 177.4 mg KOH/g; iodine value: 76.8 g I$_2$/100 g sample; polyethylene glycol: 0.57%. $^1$H NMR (δ, CDCl$_3$): 5.3 (—CH=CH—); 3.7-3.4 (—CH$_2$—CH$_2$—O—); 0.9 (CH$_3$—).

The reactor contents (3298.0 g) are re-heated to 150° C. as described above. Ethylene oxide (915 g, 2 additional moles per mole of starter; 5 moles of EO per mole of 9-dodecen-1-ol charged) is added to the feed at 145-160° C. After digesting 1 h at 150-160° C., the mixture is cooled to 60° C. and partially drained (1170.9 g removed) to recover the 5 mole ethoxylated unsaturated alcohol, A12-10. Hydroxyl value: 137.4 mg KOH/g; iodine value: 59.7 g $I_2$/100 g sample; polyethylene glycol: 0.42%. $^1$H NMR (δ, $d_4$-MeOH): 5.4 (—CH═CH—); 3.7-3.4 (—CH$_2$—CH$_2$—O—); 0.95 (CH$_3$—).

The reactor contents (3042.1 g) are re-heated to 150° C. as described above. Ethylene oxide (660 g, 2 additional moles per mole of starter; 7 moles of EO per mole of 9-dodecen-1-ol charged) is added to the feed at 145-160° C. After digesting 1 h at 150-160° C., the mixture is cooled to 60° C. and partially drained (1547.0 g removed) to recover the 7 mole ethoxylated unsaturated alcohol, A12-13. Hydroxyl value: 112.5 mg KOH/g; iodine value: 48.5 g $I_2$/100 g sample; polyethylene glycol: 0.44%. $^1$H NMR (δ, $d_4$-MeOH): 5.4 (—CH═CH—); 3.7-3.4 (—CH$_2$—CH$_2$—O—); 0.95 (CH$_3$—).

The reactor contents (2155.1 g) are re-heated to 150° C. Ethylene oxide (1535 g, 8 additional moles per mole of starter; 15 moles of EO per mole of 9-dodecen-1-ol charged) is added at 145-160° C. After digesting 1 h at 150-160° C., the mixture is cooled to 60° C. and drained to provide the 15 mole ethoxylated unsaturated alcohol, A12-16 (3680.5 g). Hydroxyl value: 63.3 mg KOH/g; iodine value: 27.7 g $I_2$/100 g sample; polyethylene glycol: 1.2%. $^1$H NMR (δ, $d_4$-MeOH): 5.4 (—CH═CH—); 3.7-3.4 (—CH$_2$—CH$_2$—O—); 0.95 (CH$_3$—).

1 Mole Ethoxylated C12 Alcohol, Ammonium Sulfate, A12-5

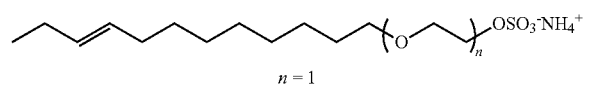
n = 1

Ethoxylated alcohol A12-4 (360 g), sulfamic acid (183.7 g), urea (6.5 g), and dioxane (700 mL) are charged to a flask and slowly heated to 105° C. After 4 h, $^1$H NMR analysis shows a complete reaction. The mixture is diluted with chloroform (500 mL), gravity filtered using a Buchner funnel and two Whatman 15-cm filter papers, then vacuum filtered to remove the urea and insoluble sulfamic acid. The filtrate is concentrated as much as possible on a rotary evaporator (1 h, 60° C.). The product is then transferred to a baking dish and dried to constant mass in a vacuum oven at 70° C. to give ether ammonium sulfate A12-5 as a viscous gel. Free oil: 0.94%. $^1$H NMR (δ, $d_4$-MeOH): 5.4 (—CH═CH—); 4.1 (—O—CH$_2$—CH$_2$—OS(O)$_2$ONH$_4$); 0.9 (CH$_3$—).

1 Mole Ethoxylated C12 Alcohol, Sodium Sulfate, A12-6

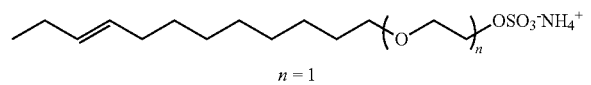
n = 1

Ether ammonium sulfate A12-5 (250 g) is charged to a round-bottom flask and diluted with methanol (500 g). An equimolar amount of sodium hydroxide (61.5 g of 50% aq. NaOH) is added slowly. The solution is concentrated on a rotary evaporator at 40° C., then at 50° C. for 2 h. The sodium sulfate compound foams during concentration, so it is transferred to a baking pan and dried in a vacuum oven (50° C., 20 mm Hg) for 4 h. The ether sodium sulfate, A12-6, is a waxy solid. Free oil: 0.82%. $^1$H NMR (δ, $d_4$-MeOH): 5.4 (—CH═CH—); 4.1 (—O—CH$_2$—CH$_2$—OS(O)$_2$ONa); 0.9 (CH$_3$—).

3 Mole Ethoxylated C12 Alcohol, Ammonium Sulfate, A12-8

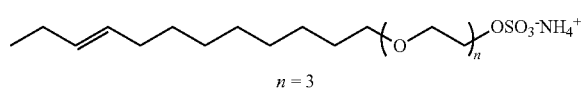
n = 3

Ethoxylated alcohol A12-7 (406.1 g, 1.28 mol) is charged to a round-bottom flask equipped with a mechanical stirrer, thermocouple, and nitrogen inlet. Sulfamic acid (103.3 g, 1.32 mol, 1.03 equiv) is added to the stirred material under nitrogen. The mixture is heated to 105° C. with vigorous stirring and sulfamic acid slowly dissolves during the reaction. After 8 h at 105° C., $^1$H NMR shows that the reaction is 98% complete. The pH is adjusted to 7.6 using NH$_4$OH. Yield of ether ammonium sulfate A12-8: 517.2 g. % Free oil (by $^1$H NMR): 5.6%. $^1$H NMR (δ, $d_4$-MeOH): 5.4 (—CH═CH—); 4.1 (—O—CH$_2$—CH$_2$—OS(O)$_2$ONH$_4$); 0.9 (CH$_3$—).

3 Mole Ethoxylated C12 Alcohol, Sodium Sulfate, A12-9

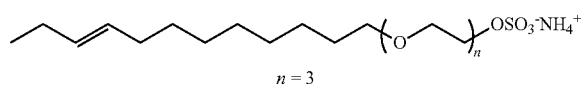
n = 3

Ethoxylated alcohol A12-7 (155 g) is charged to a 500-mL round-bottom flask equipped with a mechanical stirrer, a thermocouple, and a nitrogen inlet. Sulfamic acid (49 g) is added to the stirred material under nitrogen. The mixture is heated to 105° C. and held for 4 h. The sulfamic acid slowly dissolves during the reaction.

The reaction mixture is diluted with methanol (~450 mL), and sodium hydroxide solution (40 g of 50% aq. NaOH) is added dropwise over 30 minutes. When addition is complete, stirring continues for ~15 min, and the mixture is then cooled to room temperature. A fine white precipitate (Na$_2$SO$_4$) is filtered off, and the solid is rinsed with additional methanol. The clear yellow filtrate is concentrated to dryness on a rotary evaporator. Foaming becomes problematic at end of stripping, and drying is completed under high vacuum. The material is warmed with a heat gun to partially melt it, and full vacuum is applied to give a semi-flocculent, waxy paste. A small aliquot is dried under high vacuum for $^1$H NMR analysis, and its spectrum is consistent with the desired product. The bulk product, ether sodium sulfate A12-9, is dried overnight under full vacuum.

3 Mole Ethoxylated C14 Alcohol, Sodium Sulfate, A14-7

The procedure used to make A12-9 is generally followed starting with 9-tetradecen-1-ol to produce A14-7, an ethoxylated (3 EO) C14 alcohol sodium sulfate:

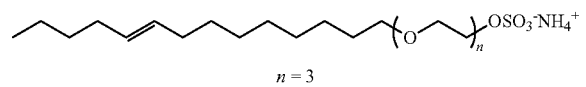
n = 3

5 Mole Ethoxylated C12 Alcohol, Ammonium Sulfate, A12-11

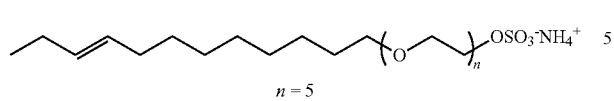
n = 5

Ethoxylated alcohol A12-10 (402 g, 0.99 mol) is charged to a round-bottom flask equipped with a mechanical stirrer, thermocouple, and nitrogen inlet. Sulfamic acid (99.4 g, 1.02 mol, 1.03 equiv) is added to the stirred material under nitrogen. The mixture is heated to 105° C. and held ~3 h with vigorous stirring, and sulfamic acid slowly dissolves during the reaction. $^1$H NMR analysis after 3 h indicates a complete reaction. Stirring at 105° C. continues for 0.5 h. The mixture is cooled to 50° C., and the pH is adjusted with NH$_4$OH via pipette. Initial pH (at 10% aq.): 2.9; final pH: 7.1. Yield of ether NH$_4$ sulfate A12-11: 498.1 g. Free alcohol CH NMR): not detected $^1$H NMR (5, CDCl$_3$): 5.4 (—CH=CH—); 4.15 (—O—CH$_2$—CH$_2$—OS(O)$_2$ONH$_4$); 0.9 (CH$_3$—).

5 Mole Ethoxylated C12 Alcohol, Sodium Sulfate, A12-12

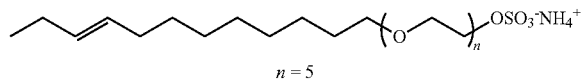
n = 5

Ether ammonium sulfate A12-11 (247.8 g) is diluted with methanol (750 mL) in a round-bottom flask, and the mixture is warmed to 35° C. Sodium hydroxide (40 g of 50% aq. NaOH) is added over 1 h with stirring. When the addition is complete, stirring continues for 30 min, and the mixture is cooled to room temperature. A fine white precipitate (Na$_2$SO$_4$) is removed, and the solid is rinsed with additional methanol. The filtrate is concentrated on a rotary evaporator at 50° C. followed by drying under high vacuum. $^1$H NMR analysis of a sample is consistent with the desired product, ether sodium sulfate A12-12, which is a viscous gel at room temperature. Yield: 260.5 g. Free alcohol (by $^1$H NMR): 0.4%. $^1$H NMR (δ, CDCl$_3$): 5.35 (—CH=CH—); 4.1 (—O—CH$_2$—CH$_2$—OS(O)$_2$ONa); 0.9 (CH$_3$—).

7 Mole Ethoxylated C12 Alcohol, Ammonium Sulfate, A12-14

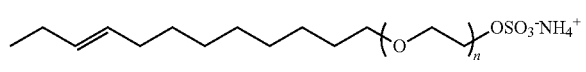
n = 7

Ethoxylated alcohol A12-13 (416 g, 0.84 mol) is charged to a round-bottom flask equipped with a mechanical stirrer, thermocouple, and nitrogen inlet. Sulfamic acid (84.4 g, 0.87 mol, 1.03 equiv) is added to the stirred material under nitrogen. The mixture is heated to 105° C. and held ~3 h, and sulfamic acid slowly dissolves during the reaction. After 3 h at 105° C., the mixture cools to room temperature under nitrogen. The mixture is reheated to 80° C., and $^1$H NMR analysis confirms a complete reaction. The viscous liquid is cooled to 50° C. for pH adjustment using aqueous NH$_4$OH. Initial pH: 3.4 (10% aqueous); final pH: 7.3. Yield of ether ammonium sulfate A12-14: 495.4 g. Free alcohol (by $^1$H NMR): not detected. $^1$H NMR (5, CDCl$_3$): 5.3 (—CH=CH—); 4.15 (—O—CH$_2$—CH$_2$—OS(O)$_2$ONH$_4$); 0.9 (CH$_3$—).

7 Mole Ethoxylated C12 Alcohol, Sodium Sulfate, A12-15

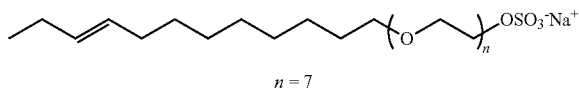
n = 7

Ether ammonium sulfate A12-14 (247.8 g) is diluted with methanol (~750 mL), and the mixture is warmed to 35° C. Sodium hydroxide (33.6 g of 50% aq. NaOH) is added dropwise over ~1 h. When the addition is complete, stirring continues for ~30 min and then the mixture is cooled to room temperature. A fine white precipitate (Na$_2$SO$_4$) is removed by filtration, and the solid is rinsed with additional methanol. The clear yellow filtrate is concentrated on a rotary evaporator at 60° C., followed by completion of drying under high vacuum. A small sample is dried under high vacuum for $^1$H NMR analysis, and it gives a spectrum consistent with the desired product. The dried alcohol sodium sulfate, A12-15, is a viscous liquid at room temperature. Yield: 249 g. Free alcohol (by $^1$H NMR): 0.4%. $^1$H NMR (δ, CDCl$_3$): 5.3 (—CH=CH—); 4.15 (—O—CH$_2$—CH$_2$—OS(O)$_2$ONa); 0.9 (CH$_3$—).

15 Mole Ethoxylated C12 Alcohol, Ammonium Sulfate, A12-17

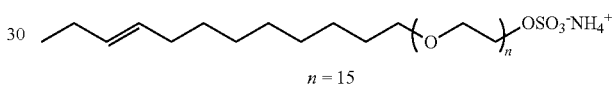
n = 15

A flask equipped with a mechanical stirrer, thermocouple, and nitrogen inlet is charged with ethoxylated alcohol A12-16 (450.2 g) and sulfamic acid (53.3 g, 0.55 mol, 1.03 equiv). The mixture is heated with strong agitation to 105° C. and held for 3 h. $^1$H NMR analysis indicates a complete reaction. The mixture is cooled to 60° C., and the pH is adjusted to neutral with ammonium hydroxide (10% aq. solution). Yield of ether ammonium sulfate A12-17: 503.5 g. Free alcohol (by $^1$H NMR): not detected. $^1$H NMR (δ, d$_4$-MeOH): 5.4 (—CH=CH—); 4.1 (—O—CH$_2$—CH$_2$—OS(O)$_2$ONH$_4$); 0.95 (CH$_3$—).

15 Mole Ethoxylated C12 Alcohol, Sodium Sulfate, A12-18

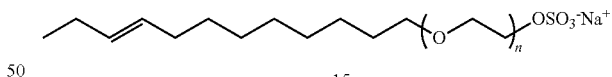
n = 15

Ether ammonium sulfate A12-17 (247.8 g) and methanol (500 mL) are charged to a round-bottom flask. The solution is warmed to 30° C., and sodium hydroxide (21.4 g of 50% aq. NaOH) is added dropwise. After the addition is complete, the material is transferred to a Büchi flask and concentrated on a rotary evaporator (40° C. to 60° C.), then dried under vacuum for 4 h. Yield of ether sodium sulfate A12-18: 230.3 g. Free alcohol (by $^1$H NMR): not detected. $^1$H NMR (δ, d$_4$-MeOH): 5.8 (CH$_2$=CH—); 4.9 (CH$_2$=CH—); 4.1 (—O—CH$_2$—CH$_2$—OS(O)$_2$ONa).

Falling-Film Sulfation of C12 Unsaturated Alcohol: Preparation of A12-99

In a batch reactor maintained at 40° C. under a nitrogen flow (5 L/min.), 9-dodecen-1-ol ("A12-1," 41.38 g, 0.225 mol), is added. Sulfur trioxide (21.54 g, 0.269 mol) is evaporated over 45 min. via a 140° C. flash-pot and is bubbled through the reactor using the nitrogen stream. The addition rate of $SO_3$ is adjusted to keep the reaction temperature at or below 50° C. At the end of the addition, the reaction mixture is maintained for an additional 5 min. to obtain a dark, viscous acid. A portion (50.1 g) of this acid is then added to a stirred solution of water (131.6 g) and 50% aqueous NaOH (18.2 g), and then the resulting solution is maintained at 70° C. for 1 h.

Analysis of the resulting composition, A12-99 reveals: 45% unsaturated primary alcohol sulfate; 40% secondary hydroxyalkyl primary alcohol sulfate; 12% sulfonates. In contrast, the preparation of A12-3 from 9-dodecen-1-ol gives almost all unsaturated primary alcohol sulfate.

Falling-Film Sulfation of C12 Unsaturated Alcohol Ethoxylate: Preparation of A12-20

The procedure used to make A12-99 is generally followed using a $C_{12}$ alcohol (2.2 EO) ethoxylate instead of 9-dodecen-1-ol. Analysis of the resulting composition, A12-20, reveals: 88% unsaturated alcohol ethoxylate sulfate, 3% secondary hydroxyalkyl alcohol ethoxylate sulfate; 5% sulfonates.

Agricultural Dispersant Screening:

The potential of a composition for use as an agricultural dispersant is evaluated by its performance with five typical pesticide active ingredients: atrazine, chlorothalonil, diuron, imidacloprid and tebuconazole. The performance of each dispersant sample is evaluated in comparison with five standard Stepsperse® dispersants: DF-100, DF-200, DF-400, DF-500, and DF-600 (all products of Stepan Company), and each is tested with an anionic wetting agent.

A screening sample is prepared as shown below for each active. Wetting agents, clays, and various additives are included or excluded from the screening process as needed. The weight percent of pesticide ("technical material") in the formulation depends on the desired active level of the final product. The active level chosen is similar to other products on the market. If this is a new active ingredient, then the highest active level is used.

Samples are evaluated in waters of varying hardness, in this case 342 ppm and 1000 ppm. The initial evaluations are performed at ambient temperature. Other temperatures can be evaluated as desired. The 342 ppm water is made by dissolving anhydrous calcium chloride (0.304 g) and magnesium chloride hexahydrate (0.139 g) in deionized water and diluting to 1 L. The 1000 ppm water is made similarly using 0.89 g of calcium chloride and 0.40 g of magnesium chloride hexahydrate.

Technical material (60-92.5 wt. %), wetting agent (0.5-1.0 wt. % when used), silica (0.5-1.0 wt. %), and clay (balance) are blended in a suitable container. The blend is milled to a particle size of at least a d(90) of <20μ using a hammer and air/jet mills as needed. Test dispersant (0.1 g) is added to test water (50 mL) in a beaker and stirred 1-2 min. Milled powder containing the technical material (1.0 g) is added to the dispersant solution and stirred until all powder is wet (2-5 min.). The mixture is transferred to a 100-mL cylinder using additional test water for rinsing the beaker and is then diluted to volume. The cylinder is stoppered and inverted ten times, then allowed to stand. Visual inspection is performed at t=0.5, 1.0, 2.0, and 24 hours, and the amount of sediment observed (in mL) is recorded. Trace of sediment="Tr"; flocked is also abbreviated as "Fl." (see Tables 2A, 2B, and 2C).

Overall results versus the controls are summarized in Table 1; fifteen samples perform at least as well as the controls; one (A12-5) is superior. Details of the individual tests are reported in Tables 2A, 2B, and 2C.

TABLE 1

Performance as an Agricultural Dispersant

| Sample | Rating |
|---|---|
| A10-5 | good |
| A10-6 | good |
| A10-8 | good |
| A10-9 | good |
| A10-11 | good |
| A10-12 | good |
| A10-14 | good |
| A10-15 | good |
| A10-17 | good |
| A10-18 | good |
| A12-5 | superior |
| A12-8 | good |
| A12-9 | good |
| A12-11 | good |
| A12-12 | good |
| A12-14 | good |
| Control | good |

TABLE 2A

Agricultural Dispersants Testing: Anionic Wetting Agent Included Sedimentation results at 1 h; 24 h (mL)

| | test water, ppm | DF-200 | DF-500 | A10-5 | A10-6 | A10-8 | A10-9 |
|---|---|---|---|---|---|---|---|
| Diuron | 342 | 0.25-0.5; 1 | Tr; 1 | 0.5; 0.75-1 | 0.25-0.5; 0.5-1 | 0.5-0.75; 1-1.25 | 0.5; 1.0-1.25 |
| | 1000 | 0.5-1; 1-1.25 | 2-2.5; 2 | 0.5-0.75; 1 | 0.5; 1 | 0.5-0.75; 1-1.25 | 0.5-0.75; 1.25-1.75 |
| Chlorothalonil | 342 | 0.25; 1.5 | Tr; 1.25 | 0.5-1.5; 2-2.25 | 0.5-0.75; 1.25-1.5 | 0.25-0.5; 1.25 | 0.75-1.0; 1.5-1.75 |
| | 1000 | Tr; 1.75 | 5; 3.5 | 0.5-0.75; 1-1.5 | 0.75; 1.5 | 0.25-0.75; 1.75-2.0 | 0.25; 0.5-0.75 |
| Imidacloprid | 342 | Tr; 1-1.5 | Tr; 1.5-2 | flocked | flocked | 4.75-5.0; Fl. | 2.75-3.0; Fl. |
| | 1000 | Tr; 2 | 1-1.5; 3 | flocked | flocked | 4.5-4.75; Fl. | 3.5-3.75; Fl. |
| Tebuconazole | 342 | 0; 1 | Tr; 1 | flocked | flocked | flocked | flocked |
| | 1000 | 0.5-1; 3.5-4 | 12; 5 | flocked | flocked | flocked | flocked |
| Atrazine | 342 | Tr; 1 | Tr; 1 | 0.25; 1.25-1.5 | 0.25-0.5; 1-1.25 | Tr-0.25; 1.25-1.5 | 0.25; 0.75-1.25 |
| | 1000 | Tr; 2 | 7; 4 | 0.25; 1-1.25 | 0.25; 1-1.25 | 0.25; 1.5-1.75 | 0.25; 1.5-2.0 |
| Rating | | control | control | good | good | good | good |

TABLE 2B

Agricultural Dispersants Testing: Anionic Wetting Agent Included Sedimentation results at 1 h; 24 h (mL)

| | test water, ppm | A10-11 | A10-12 | A10-14 | A10-15 | A10-17 | A10-18 |
|---|---|---|---|---|---|---|---|
| Diuron | 342 | 0.5; 1 | 0.5-0.75; 1.5-1.75 | 0.5-0.75; 0.75-1.0 | 0.5-0.75; 1.25-1.5 | 0.5-0.75; 1.0-1.25 | 0.5-0.75; 1.25-1.5 |
| | 1000 | 0.75; 2 | 0.75; Fl. | 1.25-1.5; Fl. | 0.5-0.75; 1.25-1.5 | 1.25-1.5; Fl. | 1.0-1.25; Fl. |
| Chlorothalonil | 342 | 0.5-0.75; 1.5-1.75 | 0.75; 1.75-2.0 | 0.25-0.75; 0.75-1.0 | 0.25-0.75; 1.5-1.75 | 0.75-1.25; 1.75-2.0 | 0.25; 1.5-1.75 |
| | 1000 | 0.5; 1-1.25 | 0.75-1.0; 1.5-1.75 | 0.25-0.5; 1.0-1.25 | 0.75-1.25; 2 | 0.5-0.75; 1.25-1.5 | 0.25; 1.0-1.25 |
| Imidacloprid | 342 | flocked | 2.0-2.25; Fl. | 4.0-4.25; Fl. | flocked | flocked | flocked |
| | 1000 | flocked | 2; Fl. | 3.75; Fl. | flocked | flocked | flocked |
| Tebuconazole | 342 | flocked | flocked | flocked | flocked | flocked | flocked |
| | 1000 | flocked | flocked | flocked | flocked | flocked | flocked |
| Atrazine | 342 | 0.5; 1.75 | 0.25; 1 | 0.25-0.5; 1.5-1.75 | 0.25-0.5; 1.0-1.25 | 0.25-0.75; 1 | 0.25; 1.0-1.25 |
| | 1000 | 0.5; 1.75-2 | 0.25; 1 | 0.25; 1.25-1.5 | Tr-0.25; 0.75-1.0 | 0.25-0.5; 1.0-1.25 | 0.25; 1.5 |
| Rating | | good | good | good | good | good | good |

TABLE 2C

Agricultural Dispersants Testing: Anionic Wetting Agent Included Sedimentation results at 1 h; 24 h (mL)

| | test water, ppm | A12-5 | A12-8 | A12-9 | A12-11 | A12-12 | A12-14 |
|---|---|---|---|---|---|---|---|
| Diuron | 342 | 0.5-0.75; 1.0-1.25 | 0.5-1.0; 1.25-2.25 | 0.5; Fl. | 1.0-1.5; 2.0-2.5 | 1.0; 2.0 | 1.0-1.25; 1.5 |
| | 1000 | 0.5; 0.75-1.0 | 2.0; Fl. | flocked | 2.0-2.25; Fl. | 1.75; Fl. | 2.25; Fl. |
| Chlorothalonil | 342 | 0.25; 1.0-1.25 | 0.5-0.75; 2.0 | 0.5-0.75; 1.25-1.5 | 0.5-1.25; 1.0-1.5 | 0.25-0.5; 0.75-1.0 | 0.5-0.75; 1.5-1.75 |
| | 1000 | 0.25-0.5; 1.0-1.25 | 0.5; 1.5-1.75 | 0.5; 1.25-1.5 | 0.75-1.5; 1.5-2.75 | 0.5-1.0; 1.0-1.5 | 0.25-0.5; 1.0-1.5 |
| Imidacloprid | 342 | 0.5; 1.0-1.5 | 0.75; 1.5 | 1.75-2; Fl. | 1.0-1.25; 2.0-2.5 | 1.0; 2.0-2.5 | 0.75; 1.75-2.0 |
| | 1000 | 1.0; Fl. | 3.25; 2.5 | flocked | 2.0-2.5; 2.0-2.5 | 3.0; 2.0-2.5 | 2.75; 2.0 |
| Tebuconazole | 342 | Tr; 0.5-0.75 | Tr; 1.25 | Tr; 1.75-2.0 | Tr; 3.0-3.25 | Tr; 3.0-3.25 | Tr; 4.0 |
| | 1000 | Tr; 1 | flocked | flocked | flocked | flocked | flocked |
| Atrazine | 342 | 0.25; 1-1.25 | 0.25-0.5; 1.0-1.5 | 0.25; 1-1.75 | 0.25-0.5; 1.0-1.25 | 0.5; 1.0-1.25 | 0.25-0.5; 1.75-2.0 |
| | 1000 | 0.25; 1.0 | 0.5-0.75; 2.0-2.25 | 0.25; 1.25-1.75 | 0.5-1.0; 1.0-2.25 | 0.25-1.0; 2.0-2.25 | 0.25-0.5; 1.0-1.5 |
| Rating | | superior | good | good | good | good | good |

Water-Soluble Herbicide Formulation Testing

Surfactant candidates for water soluble herbicide applications are examined as a replacement for the anionic, nonionic, or anionic/nonionic blend portion and compared to a known industry adjuvant standard for use in paraquat, a water soluble herbicide concentrate formulation. A standard dilution test is conducted whereby the concentrates are diluted in water to determine if solubility is complete.

Control:

Paraquat (9.13 g of 43.8% active material) is added to a 20-mL glass vial. A known industry paraquat adjuvant (2.8 g) is added and vigorously mixed for 30 s. Deionized water (8.07 g) is added, and mixing resumes for 30 s. Standard 342 ppm water (47.5 mL) is added to a 50-mL Nessler cylinder, which is stoppered and equilibrated in a 30° C. water bath. Once the test water equilibrates, the formulated paraquat (2.5 mL) is added by pipette into the cylinder. The cylinder is stoppered and inverted ten times. Solubility is recorded as complete or incomplete. Cylinders are allowed to stand and the amount (in mL) and type of separation are recorded after 30 min., 1 h, 2 h, and 24 h. Results of the solubility testing appear in Table 3 below.

Anionic Test Sample:

Paraquat (4.57 g of 43.8% active material) is added to a 20-mL glass vial. An eight to ten mole alkyl phenol ethoxylate surfactant (0.7 g) is added and vigorously mixed for 30 s. Test sample (0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Nonionic Test Sample:

Paraquat (4.57 g of 43.8% active material) is added to a 20-mL glass vial. Test sample (0.7 g) is added and vigorously mixed for 30 s. Sodium linear alkylbenzene sulfonate ("NaLAS," 0.7 g) is added and mixing resumes for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Adjuvant (Anionic/Nonionic) Test Sample:

Paraquat (4.57 g of 43.8% active material) is added to a 20-mL glass vial. Test sample (1.4 g) is added and vigorously mixed for 30 s. Deionized water (4.03 g) is added, and mixing resumes for 30 s. A 2.5-mL sample of the formulated paraquat is added to 47.5 mL of 342 ppm hardness water, and testing continues as described above for the control sample.

Criteria for emulsion solubility: Test samples should be as good as or better than the control with no separation after one hour. Nine test samples perform as well as the control in the emulsion stability test, while fifteen give a superior result. Results appear in Table 3.

TABLE 3

Water Soluble Herbicide Formulation:
Emulsion stability, mL separation

| sample | Anionic | | | Nonionic | | | Adjuvant | | | Rating |
|---|---|---|---|---|---|---|---|---|---|---|
| | sol | 1 h | 24 h | sol | 1 h | 24 h | sol | 1 h | 24 h | |
| A10-2 | S | 0 | 0 | D | 0 | Tr | S | 0 | 0 | good |
| A10-3 | S | 0 | 0 | D | 0 | Tr | S | 0 | 0 | good |
| A10-5 | S | 0 | 0 | D | 0 | Tr | S | 0 | 0 | good |
| A10-6 | S | 0 | 0 | D | 0 | Tr | S | 0 | 0 | good |
| A10-8 | S | 0 | 0 | S | 0 | 0 | S | 0 | 0 | superior |
| A10-9 | S | 0 | 0 | S | 0 | 0 | S | 0 | 0 | superior |
| A10-11 | S | 0 | 0 | S | 0 | 0 | S | 0 | 0 | superior |
| A10-12 | S | 0 | 0 | S | 0 | 0 | S | 0 | 0 | superior |
| A10-14 | S | 0 | 0 | S | 0 | 0 | S | 0 | 0 | superior |
| A10-15 | S | 0 | 0 | S | 0 | 0 | S | 0 | 0 | superior |
| A10-17 | S | 0 | 0 | S | 0 | 0 | S | 0 | 0 | superior |
| A10-18 | S | 0 | 0 | S | 0 | 0 | S | 0 | 0 | superior |
| A12-2 | S | 0 | 0 | D | 0 | 0 | D | 0 | 0 | good |
| A12-3 | S | 0 | 0 | D | 0 | Tr | D | 0 | Tr | good |
| A12-5 | S | 0 | 0 | D | 0 | 0.5 | S | 0 | 0 | good |
| A12-6 | S | 0 | 0 | D | 0 | 0 | S | 0 | 0 | good |
| A12-8 | S | 0 | 0 | I | 1 | 2.2 | S | 0 | 0 | good |
| A12-9 | S | 0 | 0 | S | 0 | 0 | S | 0 | 0 | superior |
| A12-11 | S | 0 | 0 | S | 0 | 0 | S | 0 | 0 | superior |
| A12-12 | S | 0 | 0 | S | 0 | 0 | S | 0 | 0 | superior |
| A12-14 | S | 0 | 0 | S | 0 | 0 | S | 0 | 0 | superior |
| A12-15 | S | 0 | 0 | S | 0 | 0 | S | 0 | 0 | superior |
| A12-17 | S | 0 | 0 | S | 0 | 0 | S | 0 | 0 | superior |
| A12-18 | S | 0 | 0 | S | 0 | 0 | S | 0 | 0 | superior |

D = dispersable;
S = soluble;
I = insoluble;
Tr = trace
Control result: Solubility: D; 1 h: 0 mL; 24 h: Tr.

Agricultural Products: Anionic Emulsifiers

Anionic surfactant samples contain a relatively high amount of water (>20%) and are prepared as oil-in-water (EW) concentrates. These are tested against controls containing a standard surfactant or a blank. Enough is formulated to test two water hardnesses (34 ppm and 1000 ppm) for each of the three samples.

Sample Preparation:

Pyraflufen (97.8% active, 0.30 g) is combined and with Stepan® C-25 (methyl caprylate/caprate, 7.20 g), and N-methyl-2-pyrrolidone (1.20 g), and the mixture is stirred magnetically until dissolved. In a separate container, Toximul® 8242 (castor oil ethoxylate, POE 40, product of Stepan) 0.96 g), Ninex® MT-630F (fatty acid ethoxylate, POE 30, Stepan, 0.19 g), Ninex MT-615 (fatty acid ethoxylate, POE 15, Stepan, 0.17 g), Aromatic 150 solvent (ExxonMobil, 0.37 g), and the anionic sample to be tested (0.71 g) are blended. If needed, the anionic sample is melted in an oven at 50-60° C. prior to combining with the other surfactants. When the pyraflufen has dissolved, the entire surfactant blend is added and magnetically stirred until homogeneous. Deionized water (0.90 g) is slowly added with mixing to prevent gelling. Turbidity changes are noted and recorded.

Control 1 Sample:

The same procedure is followed except that the anionic sample is replaced with Ninate® 60 L (calcium alkylbenzenesulfonate, Stepan, 0.71 g).

Control 2 Sample:

No Ninate 60 L (or anionic sample) is included, and the Aromatic 150 amount is increased to 1.08 g.

Emulsion Stability Testing

ASTM E1116-98 (2008) is modified as follows. Flat-bottomed, 100-mL graduated cylinders are charged with 34 ppm or 1000 ppm water (95 mL). A Mohr pipette is used to feed EW concentrate to each cylinder. Cylinders are stoppered and inverted ten times, then allowed to stand for 0.5, 1, and 24 h while recording stability at each time as type and % separation.

Spontaneity is recorded according to the following criteria: (1) poor: very thin emulsion cloud with major separation of oil droplets; (2) fair: thin emulsion cloud with minor separation of oil droplets; (3) good: thin emulsion cloud reaches the bottom of the cylinder without separation of any type; (4) excellent: thick emulsion cloud reaches the bottom of the cylinder without separation of any type.

Results are provided in Table 4. Each of the samples reported in the table is rated "good" overall as an anionic surfactant.

TABLE 4

Performance as an Anionic Emulsifier: % Separation

| | 34 ppm water | | | 1000 ppm water | | |
|---|---|---|---|---|---|---|
| | Spont. | 1 h | 24 h | Spont. | 1 h | 24 h |
| Control 1 | G | <0.2 C | 1.3 C | G | <0.2 C | 1.3 C |
| Control 2 | F | 4 C | 4.4 C | F | 4 C | 4.4 C |
| A10-2 | P | 3.8 C | 4 C | F | 3.1 C | 3.8 C |
| A10-3 | F | 4 C | 4 C | F | 3 C | 3.1 C |
| A10-5 | F | 3.8 CO | 4.3 CO | F | 2.8 CO | 3 CO |
| A10-6 | F | 4 CO | 4.9 CO | F | 3 CO | 3.2 CO |
| A10-8 | F | 3.5 C | 3.9 C | F | 3.5 C | 3.5 C |
| A10-9 | F | 4 C | 3.6 C | F | 3.5 C | 3.9 C |
| A10-11 | F | 3.9 CO | 5 CO | F | 2.5 CO | 3.1 CO |
| A10-12 | P | 3.6 C | 4 C | P | 3.4 C | 4.3 C |
| A10-14 | F | 3.5 C | 4 C | F | 3.5 C | 4.1 C |
| A10-15 | F | 3.5 C | 3.9 C | F | 3 C | 4.1 C |
| A10-17 | P | 1.5 C | 2.2 C | P | 1.5 C | 2 C |
| A10-18 | F | 2.5 C | 2.8 C | F | 4 C | 4 C |
| A12-2 | F | 4 C | 4.2 C | F | 2.5 C | 3.2 C |
| A12-3 | G | 4.5 C | 5.7 C | F | 3 C | 4 C |
| A12-5 | P | 4 C | 4.1 C | P | 3 C | 3.5 C |
| A12-6 | F | 4.3 C | 5.2 C | F | 2.7 C | 3.7 C |
| A12-8 | F | 3 C | 4 C | F | 3.7 C | 3.9 C |
| A12-9 | F | 3.3 CO | 4.2 CO | F | 2.1 CO | 3 CO |
| A12-11 | G | 3.6 C | 3.8 C | F | 2.1 C | 3 C |
| A12-12 | F | 4.1 C | 4.5 C | F | 3 C | 3.8 C |
| A12-14 | F | 3.9 C | 4.1 C | F | 2.8 C | 3.5 C |
| A12-15 | F | 3.5 C | 3.9 C | F | 3.5 C | 4 C |
| A12-17 | F | 4 C | 3.8 C | F | 3.5 C | 4.2 C |
| A12-18 | F | 3 C | 4.3 C | F | 2.5 C | 3.9 C |

Separation denoted in the form of a cream (C), creamy oil (CO), or oil (O).
"Spon." = spontaneity or bloom, rated as E (excellent), G (good), F (fair), P (poor).
Control 1 = native anionic; control 2 = no anionic emulsifier.

Hard-Surface Cleaners: Aqueous Degreasers

This test measures the ability of a cleaning product to remove a greasy dirt soil from a white vinyl tile. The test is automated and uses an industry standard Gardner Straight Line Washability Apparatus. A camera and controlled lighting are used to take a live video of the cleaning process. The machine uses a sponge wetted with a known amount of test product. As the machine wipes the sponge across the soiled tile, the video records the result, from which a cleaning percentage can be determined. A total of 10 strokes are made using test formulation diluted 1:32 with water, and cleaning is calculated for each of strokes 1-10 to provide a profile of the cleaning efficiency of the product. The test sample is used as a component of different control formulations depending on whether it anionic, amphoteric, or nonionic.

Anionic Test Samples:

A neutral, dilutable all-purpose cleaner is prepared from propylene glycol n-propyl ether (4.0 g), butyl carbitol (4.0 g), sodium citrate (4.0 g), Bio-Soft® EC-690 ethoxylated alcohol (1.0 g, product of Stepan), test sample (0.29 g if 100% active material), and deionized water (to 100.0 g solution). The control sample for anionic testing replaces the test sample with Stepanol® WA-Extra PCK (sodium lauryl sulfate, Stepan, 1.0 g, nominally 30% active).

Soil composition (from Gardner ASTM D4488-95 method):

Tiles are soiled with a particulate medium (50 mg) and an oil medium (5 drops). The particulate medium is composed of (in parts by weight) hyperhumus (39), paraffin oil (1), used motor oil (1.5), Portland cement (17.7), silica (18), molacca black (1.5), iron oxide (0.3), bandy black clay (18), stearic acid (2), and oleic acid (2). The oil medium is composed of kerosene (12), Stoddard solvent (12), paraffin oil (1), SAE-10 motor oil (1), Crisco® shortening, product of J.M. Smucker Co. (1), olive oil (3), linoleic acid (3), and squalene (3).

Results appear in Tables 5 and 6.

TABLE 5 thatControl Runs for Gardner Straight Line Washability Test

| | Ave. % clean after 2, 4, 6, 8, or 10 swipes | | | | |
|---|---|---|---|---|---|
| | 2 | 4 | 6 | 8 | 10 |
| Control 11 | 53.0 | 61.0 | 63.6 | 64.6 | 66.2 |
| Control 18 | 62.2 | 67.6 | 70.4 | 71.7 | 71.7 |
| Control 20 | 65.0 | 70.7 | 72.2 | 73.7 | 74.0 |
| Control 25 | 69.8 | 76.5 | 78.2 | 79.6 | 80.0 |
| Control 26 | 66.4 | 70.6 | 71.0 | 72.5 | 73.4 |
| Control 31 | 73.6 | 88.2 | 94.7 | 96.6 | 98.0 |

TABLE 6

Gardner Straight-Line Washability Anionic Test Samples

| | | | Ave. % clean | | | | | |
|---|---|---|---|---|---|---|---|---|
| Sample | Con. # | Compound class | 2 | 4 | 6 | 8 | 10 | Rating |
| A10-2 | 25 | sulfate | 68.9 | 72.1 | 73.4 | 77.1 | 78.1 | equal |
| A10-3 | 25 | sulfate | 71.8 | 75.3 | 78.1 | 81.1 | 82.2 | equal |
| A10-5 | 18 | 1 EO ether sulfate | 56.6 | 60.3 | 60.1 | 63.8 | 64.0 | equal |
| A10-9 | 11 | 3 EO ether sulfate | 46.7 | 55.2 | 57.5 | 58.1 | 61.6 | equal |
| A10-15 | 11 | 7 EO ether sulfate | 59.0 | 63.8 | 65.7 | 66.1 | 66.4 | equal |
| A12-2 | 25 | sulfate | 69.6 | 72.6 | 75.5 | 75.9 | 77.9 | equal |
| A12-5 | 26 | 1 EO ether sulfate | 52.1 | 56.9 | 60.4 | 62.3 | 63.5 | equal |
| A12-6 | 26 | 1 EO ether sulfate | 53.3 | 60.2 | 62.4 | 63.6 | 63.8 | equal |
| A12-8 | 20 | 3 EO ether sulfate | 65.0 | 70.4 | 72.0 | 73.5 | 73.5 | equal |
| A12-12 | 20 | 5 EO ether sulfate | 61.4 | 66.8 | 68.4 | 69.3 | 69.7 | equal |
| A12-14 | 20 | 7 EO ether sulfate | 63.2 | 69.2 | 69.2 | 70.9 | 71.1 | equal |
| A12-20 | 31 | 2.2 EO ether sulfate | 91.4 | 94.0 | 95.2 | 96.6 | 96.1 | equal |
| A12-99 | 31 | sulfate/hydroxyalkyl sulfate/sulfonate mixture | 81.0 | 89.3 | 90.5 | 90.9 | 92.3 | equal |

Hard-Surface Cleaners: Foaming Glass and Window Cleaner

Control: Ammonyx® LO (lauramine oxide, 0.70 g, product of Stepan, nominally 30% active) and Bio-Terge® PAS-8S (2.00 g, sodium caprylyl sulfonate, product of Stepan, nominally 38% active) are combined with isopropyl alcohol (2.50 g) and diluted to 100 mL with deionized water.

Test formulation: Anionic test sample (0.76 g if 100% active material) and Ammonyx LO (0.70 g) are combined with isopropyl alcohol (2.50 g) and diluted to 100 mL with deionized water.

Method: The test formulation is evaluated for clarity; only clear formulations are evaluated in the low film/low streak test. The test measures the ability of the cleaner to leave a streak and film-free surface on a test mirror. The test formula is applied to a mirror in a controlled quantity and wiped with a standard substrate back and forth, leaving the spread product to dry. Once dry, the mirrors are inspected and evaluated by a two-person panel. Ratings of "better than," "equal" or "worse than" the control are assigned.

Six samples, A10-2, A10-8, A12-2, A12-8, A12-12, and A12-99 perform equal to the control in the test.

Evaluation of Light-Duty Liquid Detergents: Mixer Foam Test

This method determines the amount of soil needed to render a dishwashing detergent ineffective as a cleaner. Although the method differs from the large plate method (ASTM D4009-92), it is a similar evaluation. The method involves continuously injecting a known amount of soil sample into a bowl containing warm water and a stirred dish detergent sample. An "end point" is reached at which foam is mostly gone and waves appear at the side of the bowl. Amounts are wt. % unless otherwise indicated.

Soil Preparation:

Each detergent sample is tested using two different soils, which have the following compositions:

1. ASTM D-4009-92, Soil D: Crisco® shortening (42.85%, product of J.M. Smucker Co.), spray-dried egg (14.30%), and warm (40° C.) tap water (42.85%).

2. Shell Soil: Potato powder (15.00%), deionized water (24.80%), formaldehyde (37% aqueous solution, 0.20%), whole milk (30.00%), olive oil (15.00%), and Crisco shortening (15.00%).

Dish Detergent Formulations:

Three different control formulations are used (see below). In each of the test samples, the anionic surfactant is the same as in the control, but the secondary surfactant (the fatty amine oxide in each of the three formulations) is replaced by the test surfactant. Control formulations are tested at the beginning of each day of testing.

1. Control Formulation 1 ("C1"): Tap water (97.30%), sodium alkylbenzene sulfonate, linear (2.00% actives), lauryl/myristyl amidopropylamine oxide (0.50% actives), and formaldehyde (0.20%).

2. Control Formulation 2 ("C2"): Tap water (97.30%), sodium lauryl ether sulfate, 2 moles EO (2.00% actives), lauramine oxide (0.50% actives), and formaldehyde (0.20%).

3. Control Formulation 3 ("C3"): Tap water (97.20%), sodium lauryl sulfate (1.50% actives), sodium methyl 2-sulfolaurate and disodium 2-sulfolaurate (0.50% actives), lauryl/myristyl amidopropylamine oxide (0.50% actives), anhydrous magnesium sulfate (0.10%) and formaldehyde (0.20%).

Procedure:

A pre-warmed (50° C. oven) steel mixing bowl is charged with a mixture of warm (52° C.) tap water (495.0 g) and accurately weighed (±0.01 g) detergent formulation (5.0 g). The contents are mixed using a KitchenAid® mixer and whisk attachment at speed setting 6 for 1 min. to build up foam. At the 1 minute mark, soil is dispensed continuously into the stirred mixture using a syringe pump set at 0.40 cm³/min. The amount of foam remaining is monitored, and an end point is noted at which the foam is mostly gone and the test solution makes waves against the side of the bowl. The average amount of soil added (in grams) from duplicate trials is determined for test (F1, F2, F3) and control samples (C1, C2, C3). Results appear in Tables 7A and 7B. The results in Table 7A indicate that the overall performance of alcohol sodium sulfate A14-2 equals that of the control.

All experimental samples are evaluated for their performance versus two or more controls. The experimental ammonium sulfates utilize ammonium lauryl sulfate (C1) and ammonium laureth sulfate (C2) as controls. The experimental sodium sulfates utilize sodium lauryl sulfate (C3), sodium laureth sulfate (C4), or sodium decyl sulfate (C5) as controls. In addition, mixtures of the experimental sulfates and either cocamidopropyl betaine (CB) or cocamide MEA (CM) are compared with mixtures of C1, C2, C3, C4, or C5 with either CB or CM.

Foaming properties are evaluated using a mechanical shake foam test. Sample solutions (calculated at 0.2% total surfactant active material) are thereafter made from aqueous solutions using 25° C. tap water. A 100.0-g portion of the solution is carefully transferred to a 500-mL graduated cylinder. Castor oil (2.0 g) is added. The cylinder is stoppered and mechanically inverted ten times, then allowed to

TABLE 7A

Performance as Secondary Surfactant in a Light-Duty Liquid Dish Detergent: Amount of Soil Mixture Needed to De-Foam (g)

| sample | Shell Soil | | | | | | ASTM D4009 Soil D | | | | | |
|--------|------|------|------|------|------|------|------|------|------|------|------|------|
|        | F1   | C1   | F2   | C2   | F3   | C3   | F1   | C1   | F2   | C2   | F3   | C3   |
| A14-2  | 2.95 | 3.08 | 2.86 | 3.23 | 2.57 | 2.81 | 1.42 | 1.45 | 1.32 | 1.67 | 1.24 | 1.49 |

The results in Table 7B are only comparative because the sodium ether sulfates A10-6 and A12-6 are inferior relative to the controls. However, the substantial improving trend when increasing the chain length from $C_{10}$ to $C_{12}$ suggests that similar compositions with slightly longer chain lengths, such as $C_{14}$ or $C_{16}$ sulfates or ether sulfates (e.g., see formulas below, preferably with n=0 to 20), may perform as well as the controls in this application.

settle for 15 s. Foam height is recorded. After 5 min., foam height is recorded again. The experiment is repeated without the castor oil.

In a first set of experiments, a single surfactant is used. The experimental sulfate is compared head-to-head versus each of the applicable controls at the 0.2% actives level. The results, with and without oil, are reported in each of Tables 8-14 for the initial and 5 min. foam heights.

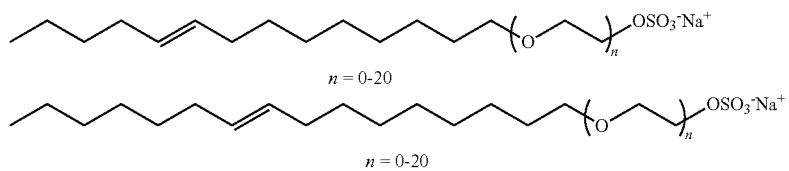

TABLE 7B

Performance as Secondary Surfactant in a Light-Duty Liquid Dish Detergent Amount of Soil Mixture Needed to De-Foam (g)

| sample | Shell Soil | | | | | | ASTM D4009 Soil D | | | | | |
|--------|------|------|------|------|------|------|------|------|------|------|------|------|
|        | F1   | C1   | F2   | C2   | F3   | C3   | F1   | C1   | F2   | C2   | F3   | C3   |
| A10-6* | 1.02 | 3.38 | 0.93 | 3.57 | 1.19 | 3.13 | 0.28 | 1.54 | 0.28 | 1.78 | 0.38 | 1.59 |
| A12-6* | 1.73 | 3.38 | 1.87 | 3.61 | 1.86 | 3.13 | 0.61 | 1.54 | 0.79 | 1.78 | 0.67 | 1.59 |

*Comparative examples.

Personal Care: Cleansing Application

A mechanical shake foam test is used to assess the likely value of a particular surfactant as a primary surfactant in personal cleansing applications.

The second set of experiments tests for possible synergistic effects when the experimental sulfate is used in combination with a small proportion of cocamidopropyl betaine (CB). In these experiments, either the control or the experimental sulfate is used at a 12:3 actives ratio with CB to evaluate the ability of CB to boost the foaming performance.

The third set of experiments tests for possible synergistic effects when the experimental sulfate is used in combination with a small proportion of cocamide MEA (CM). In these experiments, either the control or the experimental sulfate is used at a 12:1.5 actives ratio with CM to evaluate the ability of CM to boost the foaming performance.

Eight test materials, A12-2, A12-3, A12-6, A12-8, A12-9, A12-20, A12-99, and A14-2 show good overall performance in the shake foam test (see Tables 8, 9, 11-16), while one sample, A12-5, demonstrates superior performance (see Table 10).

TABLE 8

Performance of A12-2 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-2 | 390 | 350 | 310 | 150 |
| C1 | 510 | 480 | 370 | 370 |
| C2 | 440 | 440 | 360 | 360 |
| A12-2/CB (12:3) | 380 | 380 | 370 | 370 |
| C1/CB | 420 | 420 | 310 | 310 |
| C2/CB | 350 | 350 | 260 | 260 |
| A12-2/CM (12:1.5) | 320 | 320 | 290 | 290 |
| C1/CM | 420 | 420 | 310 | 310 |
| C2/CM | 370 | 370 | 310 | 310 |

Overall rating: A12-2 performs equal to controls.
C1 = ammonium lauryl sulfate;
C2 = ammonium laureth sulfate;
CB = cocamidopropyl betaine;
CM = cocamide MEA

TABLE 9

Performance of A12-3 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-3 | 350 | 350 | 310 | 110 |
| C3 | 560 | 560 | 350 | 350 |
| C4 | 440 | 440 | 350 | 350 |
| C5 | 400 | 400 | 170 | 170 |
| A12-3/CB (12:3) | 370 | 370 | 300 | 300 |
| C3/CB | 400 | 400 | 300 | 300 |
| C4/CB | 370 | 370 | 280 | 280 |
| C5/CB | 350 | 350 | 290 | 290 |
| A12-3/CM (12:1.5) | 380 | 380 | 300 | 300 |
| C3/CM | 250 | 250 | 250 | 250 |
| C4/CM | 370 | 370 | 300 | 300 |
| C5/CM | 400 | 400 | 320 | 320 |

Overall rating: A12-3 performs equal to controls.
C3 = sodium lauryl sulfate;
C4 = sodium laureth sulfate;
C5 = sodium decyl sulfate
CB = cocamidopropyl betaine;
CM = cocamide MEA

TABLE 10

Performance of A12-5 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-5 | 420 | 420 | 400 | 350 |
| C1 | 500 | 480 | 380 | 380 |
| C2 | 450 | 450 | 370 | 370 |
| A12-5/CB (12:3) | 400 | 400 | 320 | 320 |
| C1/CB | 430 | 430 | 310 | 310 |
| C2/CB | 340 | 340 | 270 | 270 |
| A12-5/CM (12:1.5) | 440 | 440 | 350 | 350 |
| C1/CM | 420 | 420 | 310 | 310 |
| C2/CM | 370 | 370 | 310 | 310 |

Overall rating: A12-5 performs superior to controls.
C1 = ammonium lauryl sulfate;
C2 = ammonium laureth sulfate;
CB = cocamidopropyl betaine;
CM = cocamide MEA

TABLE 11

Performance of A12-6 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-6 | 500 | 500 | 400 | 200 |
| C3 | 560 | 560 | 350 | 350 |
| C4 | 450 | 450 | 350 | 350 |
| A12-6/CB (12:3) | 370 | 370 | 300 | 300 |
| C3/CB | 400 | 400 | 300 | 300 |
| C4/CB | 370 | 370 | 280 | 280 |
| A12-6/CM (12:1.5) | 380 | 380 | 320 | 320 |
| C3/CM | 260 | 260 | 250 | 250 |
| C4/CM | 370 | 370 | 310 | 310 |

Overall rating: A12-6 performs equal to controls.
C3 = sodium lauryl sulfate;
C4 = sodium laureth sulfate;
CB = cocamidopropyl betaine;
CM = cocamide MEA

TABLE 12

Performance of A12-8 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-8 | 440 | 180 | 420 | 130 |
| C1 | 510 | 480 | 370 | 370 |
| C2 | 390 | 390 | 350 | 350 |
| A12-8/CB (12:3) | 350 | 350 | 300 | 300 |
| C1/CB | 420 | 420 | 310 | 310 |
| C2/CB | 340 | 340 | 270 | 270 |
| A12-8/CM (12:1.5) | 340 | 340 | 290 | 290 |
| C1/CM | 420 | 420 | 310 | 310 |
| C2/CM | 370 | 370 | 300 | 300 |

Overall rating: A12-8 performs equal to controls.
C1 = ammonium lauryl sulfate;
C2 = ammonium laureth sulfate;
CB = cocamidopropyl betaine;
CM = cocamide MEA

TABLE 13

Performance of A12-9 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-9 | 440 | 290 | 300 | 130 |
| C3 | 560 | 560 | 350 | 350 |
| C4 | 450 | 450 | 340 | 340 |
| A12-9/CB (12:3) | 360 | 360 | 300 | 300 |
| C3/CB | 400 | 400 | 300 | 300 |
| C4/CB | 370 | 370 | 280 | 280 |
| A12-9/CM (12:1.5) | 360 | 360 | 320 | 320 |
| C3/CM | 260 | 260 | 250 | 250 |
| C4/CM | 370 | 370 | 310 | 310 |

Overall rating: A12-9 performs equal to controls.
C3 = sodium lauryl sulfate;
C4 = sodium laureth sulfate;
CB = cocamidopropyl betaine;
CM = cocamide MEA

TABLE 14

Performance of A14-2 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A14-2 | 430 | 430 | 322 | 320 |
| C3 | 560 | 560 | 350 | 350 |
| A14-2/CB (12:3) | 370 | 370 | 280 | 280 |
| C3/CB | 400 | 400 | 300 | 300 |
| A14-2/CM (12:1.5) | 370 | 370 | 280 | 280 |
| C3/CM | 260 | 260 | 250 | 250 |

Overall rating: A14-2 performs equal to controls.
C3 = sodium lauryl sulfate;
CB = cocamidopropyl betaine;
CM = cocamide MEA

TABLE 15

Performance of A12-99 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-99 | 300 | 250 | 190 | 180 |
| C3 | 560 | 560 | 350 | 350 |
| C4 | 430 | 430 | 350 | 350 |
| C6 | 420 | 420 | 360 | 360 |
| A12-99/CB (12:3) | 370 | 370 | 280 | 280 |
| C3/CB | 400 | 400 | 300 | 300 |
| C4/CB | 310 | 310 | 280 | 280 |
| C6/CB | 350 | 350 | 280 | 280 |
| A12-99/CM (12:1.5) | 350 | 350 | 290 | 290 |
| C3/CM | 260 | 260 | 250 | 250 |
| C4/CM | 350 | 350 | 310 | 310 |
| C6/CM | 380 | 380 | 310 | 310 |

Overall rating: A12-99 performs equal to controls in binary systems.
C3 = sodium lauryl sulfate;
C4 = sodium laureth sulfate;
C6 = sodium laureth sulfate;
CB = cocamidopropyl betaine;
CM = cocamide MEA

TABLE 16

Performance of A12-20 as a Primary Surfactant for Personal Cleansing Foam Height (mL) in Standard Shake Foam Test

|  | No oil added | | Castor oil added | |
| --- | --- | --- | --- | --- |
|  | initial | 5 min | initial | 5 min |
| A12-20 | 460 | 200 | 400 | 150 |
| C3 | 560 | 560 | 350 | 350 |
| C4 | 430 | 430 | 350 | 350 |
| C6 | 420 | 420 | 360 | 360 |
| A12-20/CB (12:3) | 370 | 370 | 290 | 290 |
| C3/CB | 400 | 400 | 300 | 300 |
| C4/CB | 310 | 310 | 280 | 280 |
| C6/CB | 350 | 350 | 280 | 280 |
| A12-20/CM (12:1.5) | 390 | 390 | 330 | 330 |
| C3/CM | 260 | 260 | 250 | 250 |
| C4/CM | 350 | 350 | 310 | 310 |
| C6/CM | 380 | 380 | 310 | 310 |

Overall rating: A12-20 performs equal to controls in binary systems.
C3 = sodium lauryl sulfate;
C4 = sodium laureth sulfate;
C6 = sodium laureth sulfate;
CB = cocamidopropyl betaine;
CM = cocamide MEA Surfactant Phase Behavior Study:

Phase behavior is observed using an Olympus BH-2 cross-polarized microscope at 100-400× and room temperature (20° C. to 22° C.). The inventive monounsaturated sulfates and ethoxylate sulfates are compared with their saturated analogs, and in some cases, commercial surfactants.

Samples are prepared by diluting the most concentrated product gradually with deionized water. When the surfactant concentration approaches a phase transition, the concentration is varied at 2-4% intervals to estimate the phase boundary. The actives level reported in Table 15 for each phase boundary is within ±5% of the true boundary.

Samples are loaded between a microscope slide and cover glass and are allowed to equilibrate before observation. Microscopic texture is analyzed and used to determine the phase. For some samples, an AR 2000 rheometer (TA Instruments) is used to measure viscosity at 25° C. to further verify phase behavior.

At low surfactant concentrations, randomly oriented micelles (spheres or cylinders) generally predominate, resulting in a clear or isotropic liquid. As concentration increases, cylindrical micelles can arrange themselves into either hexagonal or cubic phases, both of which have very high viscosities (10-50K cP at 25° C. for the hexagonal phase, higher for the cubic phase). Thus, in the hexagonal and cubic phases, the surfactant is difficult to process or formulate. Increasing the surfactant concentration more can generate a lamellar phase, where micellar bilayers are separated by water. Because the lamellar phase is pumpable (1-15K cP at 25° C.), compositions having high levels of surfactant actives can be produced. Further concentration of the surfactant can lead to reverse micelles, in some cases generating an isotropic mixture. In sum, phase behavior is important for manufacture, processing, transportation, and formulation of compositions containing surfactants.

An ideal sample is isotropic and clear throughout the entire range of active levels with low viscosity, as this is most likely to avoid any processing issues related with gelling or precipitation during formulation. A lamellar phase is also considered favorable for processing and transportation. Less favorable gel phases include cubic, hexagonal, and solid/gum/paste. All of the sulfate and ether sulfates tested had at least some gel component. The presence of these phases at a particular actives level suggests that processing at or near that actives level will be very difficult, and precipitation of the surfactant may occur when used at or near that actives level.

Results of the microscopy study appear in Table 17. In general, the inventive ammonium salts perform similarly to their saturated analogs (see especially A10-2 versus its saturated analog), while the inventive sodium salts (A10-3 and A12-3) demonstrate differential performance when compared with the saturated analogs.

Sodium salt A10-3 has a lamellar phase from 70-81% actives, which provides an opportunity for formulating a high actives formulation and improving compaction. In contrast, the saturated analog needs to be formulated below 40% actives to avoid the hexagonal and solid/gummy phases.

Similarly, sodium salt A12-3 has a lamellar phase from 66-83% actives, providing a comfortable high-actives formulating window, while the saturated analog and the commercial alternative will normally need to be formulated at or below 30% actives to maintain good solubility and handling properties.

Ammonium salt A12-2 is similar to its saturated analog, but note the shift of the lamellar phase to a higher actives level. This provides an opportunity to formulate at low water levels, which is an advantage for improving compaction.

Sodium ethoxylate salt A12-9 is more complicated in that it provides a lamellar region in the 68-87% actives range, which favors a high active formulation, but it also has a cubic region (60-68% actives), which could potentially have some mixing difficulties during formulation.

Sodium ethoxylate salt A12-20 has a small cubic region, but it also has a favorably high proportion of isotropic clear and lamellar phases. The saturated analog of A12-9 provides a basis for comparison.

The uniquely complex mixture of alcohol sulfate, hydroxyalkyl alcohol sulfate, and sulfonates present in A12-99 results in a very favorable range of isotropic clear liquid (up to 54% actives).

In sum, the microscopy study indicates that the inventive monounsaturated compositions will offer compatibility advantages to formulators that use these surfactants, especially the monounsaturated sodium sulfates.

Thus, in one aspect, the invention includes a composition comprising a monounsaturated fatty alcohol alkali metal sulfate having at least one lamellar phase at an actives level within the range of 65-80% actives (see, e.g., A10-3, A12-3, A12-9, A12-20, and A12-99 in Table 17). Preferably, the composition has an isotropic clear phase over a broader % actives range compared with that of a composition comprising a saturated analog of the monounsaturated fatty alcohol alkali metal sulfate (see, e.g., A10-3, A12-3, and A12-9). Preferably, the composition further comprises a hydroxyalkyl alcohol sulfate and sulfonates and, more preferably, it has an isotropic clear phase at up to 50% actives (see, e.g., A12-99).

TABLE 17

Comparison of Monounsaturated Sulfates and Ether Sulfates v. Saturated Analogs: Estimated Phase Region as a Function of % Actives Level[1]

| | Isotropic Clear | Lamellar | Hexagonal | Cubic | Unknown | Solid/gum/paste |
|---|---|---|---|---|---|---|
| A10-2 (NH$_4$) | | 64-80 | 42-64 | | 0-42 | 80-100 |
| sat. analog[2] | | 64-80 | 42-64 | | 0-42 | 80-100 |
| A10-3 (Na) | 0-43 | 70-81 | 43-70 | | | 81-100 |
| sat. analog | 0-41 | | 41-59 | | | 59-100 |
| A12-2 (NH$_4$) | 0-33 | 70-83 | 33-70 | | | 83-100 |
| sat. analog | 0-31 | 63-74 | 31-63 | | | 74-100 |
| A12-3 (Na) | 0-38 | 66-83 | 38-66 | | | 83-100 |
| sat. analog | 0-31 | | | | | 31-100 |
| Stepanol ® WA-100 Extra[3] | 0-34 | | 34-55 | | | 55-100 |
| A12-9 (3 EO Na) | 0-31 | 68-87 | 31-60 | 60-68 | | 87-100 |
| sat. analog | 0-24 | 60-78 | 24-60 | | | 78-100 |
| Steol ® CS-370[4] | 0-27 | 60-72 | 27-60 | | 72-100 | |
| A12-20 (2.2 EO Na) | 0-35 | 68-88 | 35-63 | 63-68 | | 88-100 |
| A12-99 (mixture) | 0-53 | 65-81 | 53-65 | | | 81-100 |

[1] All microscopy examinations are performed at room temperature (20-22° C.). Phase boundaries are estimates.
[2] Saturated analogs prepared by catalytic hydrogenation.
[3] Stepanol ® WA-100, sodium lauryl sulfate, product of Stepan.
[4] Steol ® CS-370, sodium laureth (3EO) sulfate, product of Stepan.

Laundry Detergents: Evaluation as a Primary Anionic Surfactant

This method evaluates the ability of an experimental sample to perform as a primary anionic surfactant in a bargain laundry detergent formula that contains sodium laureth sulfate (3 moles of EO), a nonionic surfactant such as an ethoxylated synthetic $C_{12}$-$C_{15}$ alcohol (7 EO), citric acid, monoethanolamine, triethanolamine, and a preservative. The experimental surfactant replaces the alkyl ether sulfate in a standard formula and is tested for its detergency properties.

Laundry detergent formula (46 g) is charged to the laundry machine, followed by soiled/stained fabric swatches that are attached to pillowcases. Wash temperature: 90° F. Rinse: 70° F. The swatches are detached from pillowcases, dried, and ironed.

Swatches are scanned to measure the L* a* b* values, which are used to calculate a soil removal index (SRI) for each type of swatch. Finally, the ΔSRI is calculated, which equals the experimental sample SRI minus the SRI of a pre-determined standard laundry detergent formula (or control). When |ΔSRI|≥1, differences are perceivable to the naked eye. If the value of ΔSRI is greater than or equal to 1, the sample is superior. If ΔSRI is less than or equal to −1, the sample is inferior. If ΔSRI is greater than −1 and less than 1, the sample is considered equal to the standard.

The bargain laundry detergent is prepared from either the experimental sample or sodium laureth (3 EO) sulfate (Steol® CS-370, product of Stepan) (15% actives, 21.4 wt. %), Bio-Soft® N25-7 (fatty alcohol 7 EO ethoxylate, Stepan, 5.00 wt. %), citric acid (50% aq. solution, 2.00 wt. %), monoethanolamine (1.00 wt. %), triethanolamine (1.00 wt. %), and deionized water plus preservative (balance to 100 wt. %).

The formulation is made by charging 90% of the total amount of water at 50° C., then adding in order, with mixing, citric acid solution, monoethanolamine, and triethanolamine. Steol® CS-370 or experimental sample is slowly added, followed by slow addition of Bio-Soft® N25-7. Preservative and the balance of the water are then added.

The following standard soiled/stained fabric swatches are used: dust sebum on cotton (DSC); dust sebum on cotton/polyester (DSCP); beef tallow (BT); sebum tefo (ST), clay on cotton (CC); clay on cotton/polyester (CCP); grass on cotton (GC); red wine on cotton (RC); blueberry on cotton (BC); coffee on cotton (COFC); cocoa on cotton (EMPA 112); blood/ink/milk on cotton (EMPA 116); and make-up on cotton (EMPA 143). At least three of each kind of swatch are used per wash. Swatches are stapled to pillowcases for laundering, and extra pillowcases are included to complete a six-pound load.

The same procedure is used to launder all of the pillowcases/swatches, with care taken to ensure that water temperature, wash time, manner of addition, etc. are held constant for the cold-water wash process. When the cycle is complete, swatches are removed from the pillowcases, dried at low heat on a rack, and pressed briefly with a dry iron.

A Hunter LabScan® XE spectrophotometer is used to determine the L* a* b* values to calculate the SRI for every type of swatch, and the stain removal index (SRI) is calculated as follows:

$$SRI = 100 - \sqrt{(L^*_{clean} - L^*_{wahed})^2 + (a^*_{clean} - a^*_{washed})^2 + (b^*_{clean} - b^*_{washed})^2}$$

$$\Delta SRI = SRI_{sample} - SRI_{standard}$$

As shown in Table 18, A14-7 performs as well as the control sample when evaluated as primary anionic solvent for a bargain laundry detergent.

TABLE 18

Performance as a Primary Anionic Surfactant for a Bargain Detergent Formulation:
|ΔSRI| Values versus Steol® CS-370 (sodium laureth sulfate)

| test sample | ΔSRI values A14-7 |
|---|---|
| dust sebum on cotton (DSC) | 0.2 |
| dust sebum on cotton/polyester (DSCP) | 0.2 |

TABLE 18-continued

Performance as a Primary Anionic Surfactant for a Bargain Detergent Formulation:
|ΔSRI| Values versus Steol® CS-370 (sodium laureth sulfate)

| test sample | ΔSRI values A14-7 |
|---|---|
| beef tallow (BT) | 0.5 |
| sebum tefo (ST) | 0.8 |
| clay on cotton (CC) | 0.0 |
| clay on cotton/polyester (CCP) | 0.0 |
| grass on cotton (GC) | 0.7 |
| red wine on cotton (RWC) | −0.4 |
| blueberry on cotton (BC) | −0.5 |
| coffee on cotton (COFC) | −0.5 |
| cocoa on cotton (EMPA 112) | 0.6 |
| blood/ink/milk on cotton (EMPA 116) | 0.1 |
| make-up on cotton (EMPA 143) | 0.1 |
| overall rating | good |

Performance as a Foamer or Foam Additive for Specialty Foamer Applications

Specialty foamer applications include (among others) gypsum, concrete, and firefighting foams. The tests below evaluate foam stability when the sample is used as the primary foamer and also evaluate the sample's performance as an additive when used as a foam stabilizer, enhancer, or destabilizer.

Particularly for gypsum, for which set-up times are rapid on commercial production lines, a desirable foam additive helps to control the coalescence of the bubble to provide a larger bubble within a prescribed time frame. Preferably, destabilization of the foam occurs at the end of the first minute in the tests below. These compositions are identified as "good" performers as gypsum foam destabilizers in Table 19 because they allow this balance to be struck effectively.

Foam Stability: Drainage Method

Surfactant solutions (0.4 wt. % active material) are prepared by mixing surfactant with waters having varying hardnesses (342 ppm hard water or 1000 ppm CaSO₄ water). Surfactant solution (100 mL) is carefully transferred to a stainless-steel mixing cup, then mixed at high speed (27K rpm) using a Hamilton Beach mixer for 10 s. The contents are quickly poured into a 100-mL graduated cylinder to the 100-mL mark, and a stopwatch is immediately started. The amount of liquid settling in the cylinder is recorded every 15 s for 4 min. Less liquid drained indicates greater foam stability.

TABLE 19

Evaluation as Potential Foamers for Gypsum: Liquid Volume (mL) vs. Drain Time (min) in 342 ppm Hard Water

| | Drain time (min) | | | | | | | | |
|---|---|---|---|---|---|---|---|---|---|
| | 0.5 | 1.0 | 1.5 | 2.0 | 2.5 | 3.0 | 3.5 | 4.0 | Rating |
| Control | 0.25 | 1.00 | 2.00 | 3.00 | 4.00 | 5.25 | 6.50 | 7.50 | — |
| Foamer A | 0.25 | 1.00 | 2.25 | 3.00 | 4.00 | 5.00 | 6.00 | 7.00 | — |
| A10-2 | 0.75 | 2.00 | 3.50 | 5.25 | 6.75 | 8.75 | 10.50 | 12.25 | good |
| A10-3 | 3.00 | 5.75 | 8.00 | 10.25 | 12.50 | 14.50 | 16.00 | 17.75 | good |
| A10-5 | 0.0 | 0.50 | 2.00 | 3.00 | 4.50 | 5.50 | 7.00 | 8.50 | good |
| A10-6 | 0.25 | 0.75 | 2.25 | 3.25 | 5.00 | 6.25 | 7.75 | 9.25 | good |
| A10-8 | 0.0 | 0.50 | 1.75 | 3.00 | 4.25 | 5.75 | 7.25 | 9.00 | good |
| A10-9 | 0.0 | 0.50 | 2.25 | 3.25 | 4.75 | 6.00 | 7.50 | 9.25 | good |
| A10-11 | 0.0 | 0.50 | 2.25 | 3.25 | 4.75 | 6.25 | 7.75 | 9.25 | good |

TABLE 19-continued

Evaluation as Potential Foamers for Gypsum: Liquid Volume
(mL) vs. Drain Time (min) in 342 ppm Hard Water

| | Drain time (min) | | | | | | | | |
|---|---|---|---|---|---|---|---|---|---|
| | 0.5 | 1.0 | 1.5 | 2.0 | 2.5 | 3.0 | 3.5 | 4.0 | Rating |
| A10-12 | 0.0 | 0.50 | 2.25 | 3.25 | 5.00 | 6.25 | 8.00 | 9.25 | good |
| A10-14 | 0.25 | 0.75 | 2.25 | 3.75 | 5.25 | 6.75 | 8.50 | 10.25 | good |
| A10-15 | 0.25 | 1.00 | 2.50 | 3.75 | 5.25 | 6.75 | 8.50 | 10.50 | good |
| A10-17 | 0.50 | 2.25 | 3.75 | 5.50 | 7.25 | 9.25 | 11.25 | 13.25 | good |
| A10-18 | 0.25 | 1.75 | 3.25 | 5.00 | 6.50 | 8.50 | 10.25 | 12.00 | good |
| A12-2 | 0.0 | 0.25 | 1.50 | 2.50 | 3.50 | 5.00 | 6.00 | 7.50 | superior |
| A12-3 | 0.0 | 0.25 | 0.75 | 2.25 | 3.00 | 4.00 | 5.25 | 6.50 | superior |
| A12-5 | 0.0 | 0.25 | 0.75 | 2.25 | 3.25 | 4.25 | 5.50 | 7.00 | superior |
| A12-6 | 0.0 | 0.25 | 0.75 | 2.25 | 3.25 | 4.50 | 6.00 | 7.00 | superior |
| A12-8 | 0.0 | 0.25 | 1.75 | 2.50 | 3.50 | 4.75 | 6.00 | 7.25 | superior |
| A12-9 | 0.0 | 0.25 | 0.75 | 2.00 | 3.25 | 4.50 | 5.75 | 7.00 | superior |
| A12-11 | 0.0 | 0.50 | 1.50 | 2.50 | 3.75 | 5.00 | 6.25 | 7.50 | good |
| A12-12 | 0.0 | 0.25 | 1.00 | 2.25 | 3.50 | 4.50 | 6.00 | 7.25 | good |
| A12-14 | 0.0 | 0.25 | 2.00 | 2.75 | 4.00 | 5.25 | 6.50 | 8.00 | good |
| A12-15 | 0.0 | 0.50 | 1.75 | 2.75 | 3.75 | 5.25 | 6.50 | 8.00 | good |
| A12-17 | 0.25 | 0.75 | 2.25 | 3.75 | 5.25 | 7.00 | 9.00 | 10.50 | good |
| A12-18 | 0.0 | 0.75 | 2.50 | 3.50 | 5.00 | 6.75 | 8.50 | 10.00 | good |
| A12-20 | 0.0 | 0.0 | 0.75 | 2.00 | 3.00 | 4.00 | 5.25 | 6.75 | good |

Gas Well Foamers: Batch Dynamic Test

In this procedure, test surfactant, brine, and/or condensate are added to a column and then agitated with nitrogen to produce foam. The wt. % of foam carried over the column after 5 min. is a measure of the test sample's performance. Results are collected as a function of brine composition, concentration of surfactant, and percent condensate present in the solution.

Brines are prepared at 12.5% and 25% total dissolved solids (TDS). The brines are an 80:20 ratio of NaCl to $CaCl_2$. The density of the 12.5% TDS is 1.087 g/mL and the density of the 25% TDS is 1.184 g/mL. Brine solutions are filtered to eliminate particulates.

Surfactant samples are tested at 5000, 2000, 1000, and 500 parts per million of actives in each of the brine solutions listed above. A test solution consists of brine, surfactant, and condensate when applicable. The equation below indicates how much surfactant is needed based on actives level and the density of the brine used.

$$\text{Surfactant (g)} = \frac{\left[\frac{\text{desired ppm}}{1000}\right]}{\text{actives}} \times \frac{\left[\frac{\text{Total Sol'n (g)}}{\text{Density of Brine (g/mL)}}\right]}{1000}$$

This sample calculation shows how much of a 45% active surfactant is needed to make a 5000 ppm solution in 12.5% TDS brine:

$$\frac{\left[\frac{5000 \text{ ppm}}{1000}\right]}{0.45 \text{ actives}} \times \frac{\left[\frac{238.053 \text{ g}}{1.087 \text{ g/mL}}\right]}{1000} =$$

2.43 g of Surfactant into 238.053 g of 12.5% TDS brine

The 5000 ppm solution is used to make a 2000 ppm solution, which is diluted to make a 1000 ppm solution, and so on. When condensate is included, the desired active level in the brine should be such that the active level in the total test solution remains constant with the varying amounts of condensate present. For example, when making a 5000 ppm solution with 10% condensate, the brine/surfactant solution will actually be 5556 ppm so that the solution plus condensate will be ~5000 ppm. When testing how well a product handles condensate, either 10% or 20% is added to a solution. This is done for both brine solutions at every concentration level.

The condensate used is a low-aromatic mineral spirit, Exxsol® D-40 (d=0.7636 g/mL), product of ExxonMobil. The desired amount of condensate is added to the column after the brine/surfactant solution is added. Nitrogen is fed through a glass frit in the bottom of the column and a mass-flow controller is used to feed 14 standard cubic feet per hour. DataStudio (from Pasco) software and a balance are used to measure the amount of foam collected. Weight is recorded every second over the course of a 10-minute run. The % of liquid carried over as foam after 5 min. for each brine solution at each % condensate level is reported in Table 20.

As shown in Table 20, two of the test samples, A10-11 and A10-14, are superior to the control when evaluated as potential gas well foamers.

TABLE 20

Performance in Gas Well Foamers

| | | | % Carry Over at 5 min. | |
|---|---|---|---|---|
| % TDS brine | % Condensate | Conc, ppm | A10-11 | A10-14 |
| 12.5 | 0 | 500 | 49 | 52 |
| 12.5 | 10 | 500 | 66 | 63 |
| 12.5 | 20 | 500 | 57 | 42 |
| 25.0 | 0 | 500 | 41 | 39 |
| 25.0 | 10 | 500 | 0 | 0 |
| 25.0 | 20 | 500 | 0 | 0 |
| 12.5 | 0 | 1000 | 60 | 61 |
| 12.5 | 10 | 1000 | 61 | 62 |
| 12.5 | 20 | 1000 | 52 | 54 |
| 25.0 | 0 | 1000 | 55 | 55 |
| 25.0 | 10 | 1000 | 0 | 11 |
| 25.0 | 20 | 1000 | 0 | 0 |
| 12.5 | 0 | 2000 | 80 | 79 |
| 12.5 | 10 | 2000 | 70 | 70 |
| 12.5 | 20 | 2000 | 64 | 56 |
| 25.0 | 0 | 2000 | 69 | 68 |

TABLE 20-continued

Performance in Gas Well Foamers

| | | | % Carry Over at 5 min. | |
|---|---|---|---|---|
| % TDS brine | % Condensate | Conc, ppm | A10-11 | A10-14 |
| 25.0 | 10 | 2000 | 26 | 45 |
| 25.0 | 20 | 2000 | 2 | 25 |
| 12.5 | 0 | 5000 | 97 | 82 |
| 12.5 | 10 | 5000 | 80 | 81 |
| 12.5 | 20 | 5000 | 75 | 77 |
| 25.0 | 0 | 5000 | 84 | 82 |
| 25.0 | 10 | 5000 | 53 | 57 |
| 25.0 | 20 | 5000 | 34 | 49 |
| Rating | | | superior | superior |

Solubility Evaluation: Enhanced Oil Recovery (EOR)

Derivatives are evaluated as the main surfactant in control formulations to determine likely solubility performance in an EOR application. Samples are prepared in a 10% stock solution and evaluated at 1 wt. % with a brine concentration of 1% sodium chloride. Replicate experiments are performed at each temperature with each sample. Results appear in Table 21.

TABLE 21

Solubility Evaluation for EOR Applications

| Sample | Temperature (° C.) | Soluble? | Comments |
|---|---|---|---|
| control | 20.7 | yes | clear, colorless |
| A10-8 | 20.7 | yes | clear, colorless |
| control | 51.5 | yes | clear, colorless |
| A10-8 | 51.5 | yes | clear, colorless |
| control | 56.1 | yes | clear, colorless |
| A10-8 | 56.1 | yes | clear, colorless |

Overall performance of A10-8: Equal to control
Control = ammonium alkyl ether sulfate Emulsion Polymerization Surfactant Screen:

A reaction kettle is charged with sodium bicarbonate (0.50 g), water (225 g), and seed latex (30 g) and the mixture is heated to and held at 83° C. under nitrogen with stirring at 200 rpm. In a 1-L beaker, surfactant A12-3 (2.68 g, 93.3% active, 0.50% active surfactant based on total monomer) and water (150 g) are combined and stirred. Methyl methacrylate (255 g), butyl acrylate (235 g), and methacrylic acid (10 g) are combined in an Erlenmeyer flask and mixed. The monomer mixture is added to the beaker containing water and A12-3 with increasing agitator speed, and the resulting mixture is stirred 10 min. or until completely emulsified to give a monomer emulsion. Separately, two other mixtures are prepared: an initiator shot mixture of ammonium persulfate (1.0 g) in water (20 g), and a cofeed mixture of ammonium persulfate (2.70 g), sodium bicarbonate (1.50 g), and water (75 g); the total amount of initiator used is 0.74% based on monomers. The initiator shot is charged to the 83° C. reaction kettle dropwise over 1 min, then held for 10 min. The monomer emulsion is then fed to the kettle at 2.1 mL/min. for 10 min. The feed rate of the monomer emulsion is increased to 4.2 mL/min., and the cofeed mixture is started at 0.37 mL/min. Total addition time is 3 h, during which particle size and temperature are monitored. After addition of the monomer emulsion is complete, a water wash (50 g) is started, and heating at 83° C. continues for 1 h. The product is cooled. The pH is adjusted to 7.5 with dilute ammonium hydroxide solution. A preservative is added, and the mixture is filtered. Results appear in Table 22. The latex formulated using A12-3 is considered equal to the controls and suitable for use in formulating a latex paint.

TABLE 22

Evaluation as a Surfactant in Emulsion Polymerization

| | surfactant level in EP (%) | pre-emulsion stability | coag-ulum (%) | Particle size (nm) | | | |
|---|---|---|---|---|---|---|---|
| | | | | 0.5 h | 1.0 h | 2.0 h | Final |
| Control 1 | 0.50 | stable | 0.01 | 125 | 152 | 189 | 210 |
| Control 2 | 0.50 | stable | 0.04 | 137 | 165 | 214 | 235 |
| A12-3 | 0.50 | stable | 0.08 | 126 | 153 | 190 | 208 |

Control 1: sodium lauryl sulfate;
Control 2: $C_{12}$ sulfate, high purity $C_{12}$, saturated;
A12-3: $C_{12}$ sulfate, high purity $C_{12}$, unsaturated Foam Test for Agricultural Herbicides:

CIPAC Method 47.1 ("Persistent Foam Test") is generally followed. Thus, a 100-mL glass cylinder is charged with standard water D (342 ppm hardness, 95 mL). The formulation to be tested (1.0 g, 1% formulation blend) is then added, and the mixture is diluted to the 100-mL mark with additional 342 ppm water. The cylinder is stoppered and inverted 30 times. Immediately thereafter, a stopwatch is started. The amount of foam present in the cylinder (in mL) after 10 s, 1 min., 3 min., and 12 min. is recorded (see Table 23).

Results are also reported for the similar test method described in U.S. Pat. No. 5,332,714. In this method, a 250-mL cylinder is used. The cylinder is charged with 342 ppm water (190 mL), and 10 mL of the formulation to be tested is added. The cylinder is sealed and inverted 10 times. The amount of foam present in the cylinder (in mL) after 10 s, 1 min., 3 min., and 12 min. is recorded (see Table 23).

The results suggest that two derivatives, A12-20 and A12-99 are equal to the control, sodium laureth sulfate.

TABLE 23

Results of Foam Test for Surfactants for Agricultural Herbicides

| | Foam remaining (mL) | | |
|---|---|---|---|
| | Control[1] | A12-20 | A12-99 |
| Persistent Foam Test | | | |
| 10 s | 37.5 | 37.0 | 37.5 |
| 1 min | 36.0 | 36.0 | 36.0 |
| 3 min | 36.0 | 35.5 | 36.0 |
| 12 min | 36.0 | 35.5 | 36.0 |
| U.S. Pat. No. 5,332,714 Foam Test | | | |
| 10 s | 102.0 | 101.0 | 101.0 |
| 1 min | 98.0 | 97.0 | 99.0 |
| 3 min | 97.0 | 97.0 | 97.0 |
| 12 min | 97.0 | 96.0 | 97.0 |
| Rating vs. control | | equal | equal |

[1]Sodium laureth sulfate, 70% actives

Zein Test

The zein test is based on solubilization by surfactants of a yellow corn (maize) protein that is normally insoluble in water unless it is denatured. The test gravimetrically determines the amount of zein dissolved by a surfactant solution. The solubility of zein in surfactant solutions correlates well with skin irritation or roughness caused by the surfactant. The "zein number" is a value relative to a normalized control, i.e., a 1% actives solution of Stepanol® WA-Extra PCK (sodium lauryl sulfate) or Steol® CS-230 (sodium laureth sulfate) in water. A higher zein number corresponds to a greater degree of irritation.

A 1% actives solution of each test surfactant (120 mL) is prepared. The pH of each solution is adjusted to about 7.0 with dilute aq. sulfuric acid or dilute aq. sodium hydroxide. The surfactant solution is warmed to 45° C. Zein powder (1.50 g) is added to each of three jars. Surfactant (25.0 g of 1% actives solution) is added to each jar, and to one empty jar to be used as a blank. The solutions are mixed using magnetic stirring on a temperature-controlled hotplate at 45° C. for 60 min. Each mixture is then centrifuged (2500 rpm, 15 min.), and undissolved zein powder is isolated by vacuum filtration. The residue is washed with deionized water and dried (55° C., 24 h) to constant weight. The amount of undissolved zein protein is found gravimetrically, and the results from three runs are averaged to give the % of solubilized zein and zein number. Results appear in Table 24.

TABLE 24

Results of Zein Test[1]

| | % solubilized zein | zein number | comment |
|---|---|---|---|
| Stepanol ® WA-Extra PCK (SLS) | 51.4 | 100 | control |
| A12-99 | 14.0 | 27.2 | A12-99 is much less irritating than the SLS control |
| Steol ® CS-230 (SLES) | 31.0 | 60.3 | control |
| A12-20 | 22.9 | 44.6 | A12-20 is less irritating than the SLES control |

[1]Average of three runs

As shown in Table 24, the sulfated derivatives are less or much less irritating than the applicable controls, suggesting that the A12-99 and A12-20 could have value in personal care and other surfactant applications for which skin irritation is a concern.

The preceding examples are meant only as illustrations; the following claims define the invention.

We claim:
1. A sulfate composition comprising:
  (a) 40 to 60 wt. % of a monounsaturated $C_{10}$ or $C_{12}$ primary alcohol sulfate of the formula

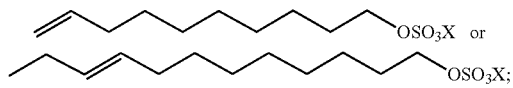

(b) 40 to 60 wt. % of a $C_{10}$ or $C_{12}$ secondary hydroxyalkyl primary alcohol sulfate of the formula

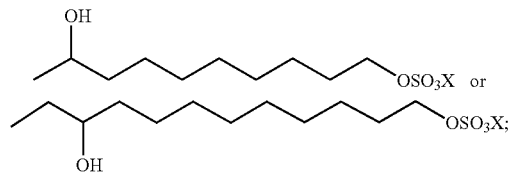

and
  (c) 0.1 to 20 wt. % of sulfonated products;
  wherein X in each formula is a mono- or divalent cation or an ammonium or substituted ammonium cation;
  wherein the sulfate composition is made by falling-film sulfation using sulfur trioxide of a $C_{10}$ or $C_{12}$ monounsaturated primary alcohol of the formula

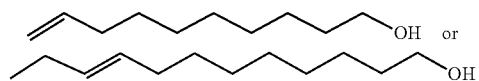

and
  wherein cross-polarized light microscopy examination at 100× to 400× and 20-22° C. of aqueous mixtures comprising the sulfate composition reveals an isotropic clear phase at all actives levels up to 50 wt. % actives.

2. The sulfate composition of claim 1 comprising 45 to 55 wt. % of the monounsaturated $C_{10}$ or $C_{12}$ primary alcohol sulfate and 45 to 55 wt. % of the $C_{10}$ or $C_{12}$ secondary hydroxyalkyl primary alcohol sulfate.

3. The sulfate composition of claim 1 comprising 0.5 to 15 wt. % of sulfonated products.

4. The sulfate composition of claim 1 wherein the microscopy examination reveals a lamellar phase at actives levels within the range of 65 to 80 wt. % actives.

5. A dispersant for agricultural compositions comprising the sulfate composition of claim 1.

* * * * *